(12) United States Patent
Hitko

(10) Patent No.: US 9,447,450 B2
(45) Date of Patent: Sep. 20, 2016

(54) RED-SHIFTED LUCIFERINS AND METHODS OF USING SAME

(71) Applicant: PROMEGA CORPORATION, Madison, WI (US)

(72) Inventor: Carolyn Woodroofe Hitko, Grover Beach, CA (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

(21) Appl. No.: 14/200,563

(22) Filed: Mar. 7, 2014

(65) Prior Publication Data

US 2014/0304842 A1    Oct. 9, 2014

Related U.S. Application Data

(60) Provisional application No. 61/777,208, filed on Mar. 12, 2013.

(51) Int. Cl.
| | |
|---|---|
| C07D 277/84 | (2006.01) |
| C07D 417/04 | (2006.01) |
| C07D 417/14 | (2006.01) |
| C07D 513/04 | (2006.01) |
| C07D 513/14 | (2006.01) |
| C07D 513/22 | (2006.01) |
| C12Q 1/66 | (2006.01) |

(52) U.S. Cl.
CPC .............. *C12Q 1/66* (2013.01); *C07D 277/84* (2013.01); *C07D 417/04* (2013.01); *C07D 417/14* (2013.01); *C07D 513/04* (2013.01); *C07D 513/14* (2013.01); *C07D 513/22* (2013.01)

(58) Field of Classification Search
USPC ........................................................ 548/150
See application file for complete search history.

(56) References Cited

U.S. PATENT DOCUMENTS

| | | | |
|---|---|---|---|
| 5,998,204 A | 12/1999 | Tsien et al. | |
| 7,910,087 B2 | 3/2011 | Miller | |
| 7,951,550 B2 * | 5/2011 | Cali et al. | 435/8 |
| 2011/0033878 A1 | 2/2011 | Maki et al. | |
| 2011/0256564 A1 * | 10/2011 | Van Lune | 435/8 |
| 2013/0045497 A1 | 2/2013 | Klaubert et al. | |

FOREIGN PATENT DOCUMENTS

| | | |
|---|---|---|
| EP | 1935986 | 6/2008 |
| EP | 2277872 | 1/2011 |
| WO | WO 2010/021686 | 2/2010 |

OTHER PUBLICATIONS

Paquette, Leo A.; "Principles of Modern Heterocyclic Chemistry" (W.A. Benjamin, New York, 1968), particularly Chapters 1, 3, 4, 6, 7, and 9, Contents Pages Only.
Weissberger, "The Chemistry of Heterocyclic Compounds, A Series of Monographs" (John Wiley & Sons, New York, 1950 to present), in particular vols. 13, 14, 16, 19, and 28, Preface and Contents Pages Only.
International Union of Pure and Applied Chemistry, "Definitive Rules for Nomenclature of Organic Chemistry" J. Am. Chem. Soc. 1957, vol. 82, 5545-5574.
Berge et al., "Pharmaceutical Salts," J. Pharm. Sci., 66:1-19 (1977).
Cuadro, A. M.; Alvarez-Builla, J., "4,5-Dichloro-1,2,3-dithiazolium Chloride (Appel's Salt): Reactions with N-nucleophiles." Tetrahedron 1994, 50(33), 10037-10046.
Cho, et al., "Combinatorial synthesis of a triphenylmethine library and their application in the development of Surface Enhanced Raman Scattering (SERS) probes," Chem Comm 2010, 46, 722-724.
Shapiro et al., "A set of multicolored Photinus pyrolis luciferase mutants for in vivo bioluminescence applications" Protein Engineering, Design & Selection vol. 18 No. 12 pp. 581-587, 2005.
Davis, Audrey L., "Improved Red-emitting Firefly Luciferase Mutant for Biotechnical Applications" (2009). Chemistry Honors Papers. Paper 5, pp. 1-34. http://digitalcommons.conncoll.edu/chemhp/5.
Branchini et al., "Red- and green-emitting firefly luciferase mutants for bioluminescent reporter applications" Oct. 1, 2005;345(1):140-148.
Reddy et al., "Robust Light Emission from Cyclic Alkylaminoluciferin Substrates for Firefly Luciferase" J Am Chem Soc 2010 132(39), 13586-13587.
Branchini et al., "Naphthyl- and quinolylluciferin: green and red light emitting firefly luciferin analogues" May 1989;49(5):689-695.
Conley et al., "A Selenium Analogue of Firefly D-Luciferin with Red-Shifted Bioluminescence Emission" Angew. Chem. Int. Ed. 2012, 51, 3350-3353.
PCT International Search Report and Written Opinion for Application No. PCT/US2014/021678 dated Jun. 10, 2014 (10 pages).

* cited by examiner

*Primary Examiner* — Laura L. Stockton
(74) *Attorney, Agent, or Firm* — Michael Best & Friedrich LLP

(57) ABSTRACT

Novel red-shifted luciferin derivatives and uses of those compounds are provided.

22 Claims, 14 Drawing Sheets

*Clinical signs and animal behavior*

Table 1: Clinical signs in groups 1-10 from day 0 to 4

| Group | Animal no. | Fate | Observation | Study Days Observed |
|---|---|---|---|---|
| Group 01: Vehicle | 001 | A | Normal | 0, 1, 2, 3, 4 |
| | 002 | A | Normal | 0, 1, 2, 3, 4 |
| | 003 | A | Normal | 0, 1, 2, 3, 4 |
| | 004 | A | Normal | 0, 1, 2, 3, 4 |
| Group 02: 4739 - 18mg/kg | 005 | A | Normal | 0, 1, 2, 3, 4 |
| | 006 | A | Normal | 0, 1, 2, 3, 4 |
| | 007 | A | Normal | 0, 1, 2, 3, 4 |
| | 008 | A | Normal | 0, 1, 2, 3, 4 |
| Group 03: 4739 - 35mg/kg | 009 | A | Normal | 0, 1, 2, 3, 4 |
| | 010 | A | Normal | 0, 1, 2, 3, 4 |
| | 011 | A | Normal | 0, 1, 2, 3, 4 |
| | 012 | A | Normal | 0, 1, 2, 3, 4 |
| Group 04: 4739 - 88mg/kg | 013 | A | Normal | 0, 1, 2, 3, 4 |
| | 014 | A | Normal | 0, 1, 2, 3, 4 |
| | 015 | A | Normal | 0, 1, 2, 3, 4 |
| | 016 | A | Normal | 0, 1, 2, 3, 4 |
| Group 05: 4813 - 19mg/kg | 017 | A | Normal | 0, 1, 2, 3, 4 |
| | 018 | A | Normal | 0, 1, 2, 3, 4 |
| | 019 | A | Normal | 0, 1, 2, 3, 4 |
| | 020 | A | Normal | 0, 1, 2, 3, 4 |
| Group 06: 4813 - 71mg/kg | 021 | A | Normal | 0, 1, 2, 3, 4 |
| | 022 | A | Normal | 0, 1, 2, 3, 4 |
| | 023 | A | Normal | 0, 1, 2, 3, 4 |
| | 024 | A | Normal | 0, 1, 2, 3, 4 |
| Group 07: 4813 - 141mg/kg | 025 | A | Normal | 0, 1, 2, 3, 4 |
| | 026 | A | Normal | 0, 1, 2, 3, 4 |
| | 027 | A | Normal | 0, 1, 2, 3, 4 |
| | 028 | A | Normal | 0, 1, 2, 3, 4 |
| Group 08: Reference compound - 13mg/kg | 029 | A | Normal | 0, 1, 2, 3, 4 |
| | 030 | A | Normal | 0, 1, 2, 3, 4 |
| | 031 | A | Normal | 0, 1, 2, 3, 4 |
| | 032 | A | Normal | 0, 1, 2, 3, 4 |
| Group 09: Reference compound - 55mg/kg | 033 | A | Normal | 0, 1, 2, 3, 4 |
| | 034 | A | Normal | 0, 1, 2, 3, 4 |
| | 035 | A | Normal | 0, 1, 2, 3, 4 |
| | 036 | A | Normal | 0, 1, 2, 3, 4 |
| Group 10: Reference compound - 133mg/kg | 037 | A | Normal | 0, 1, 2, 3, 4 |
| | 038 | A | Normal | 0, 1, 2, 3, 4 |
| | 039 | A | Normal | 0, 1, 2, 3, 4 |
| | 040 | A | Normal | 0, 1, 2, 3, 4 |

FIG. 6

Table 2: Survival rate in groups 1-10 until end of experimental phase

| Group | Alive |
|-------|---------|
| 1 | 100.00% |
| 2 | 100.00% |
| 3 | 100.00% |
| 4 | 100.00% |
| 5 | 100.00% |
| 6 | 100.00% |
| 7 | 100.00% |
| 8 | 100.00% |
| 9 | 100.00% |
| 10 | 100.00% |

FIG. 7

*Body weights*

Table 3: Body weights [g] in groups 1-10 on days 0 to 4

| Group | Animal ID | 03.06.2013 0 | 04.06.2013 1 | 05.06.2013 2 | 06.06.2013 3 | 07.06.2013 4 |
|---|---|---|---|---|---|---|
| 1 | 001 | 27.60 | 27.70 | 27.90 | 28.40 | 29.30 |
|   | 002 | 24.50 | 24.50 | 24.90 | 24.70 | 25.30 |
|   | 003 | 26.20 | 26.40 | 26.50 | 26.60 | 26.80 |
|   | 004 | 25.40 | 25.70 | 27.00 | 26.70 | 27.10 |
| 2 | 005 | 27.30 | 26.80 | 27.20 | 26.60 | 26.40 |
|   | 006 | 27.20 | 26.40 | 28.00 | 27.40 | 26.60 |
|   | 007 | 28.30 | 27.20 | 27.70 | 27.90 | 28.80 |
|   | 008 | 26.20 | 24.60 | 25.30 | 26.10 | 26.20 |
| 3 | 009 | 30.50 | 29.20 | 30.30 | 31.00 | 31.60 |
|   | 010 | 26.90 | 26.30 | 26.70 | 26.20 | 26.20 |
|   | 011 | 31.40 | 30.10 | 32.30 | 32.20 | 33.70 |
|   | 012 | 27.30 | 27.10 | 27.20 | 26.70 | 28.00 |
| 4 | 013 | 25.40 | 24.20 | 25.60 | 26.10 | 25.90 |
|   | 014 | 27.80 | 27.60 | 29.60 | 28.60 | 28.40 |
|   | 015 | 25.80 | 24.40 | 24.90 | 25.30 | 25.40 |
|   | 016 | 27.90 | 25.90 | 27.60 | 28.50 | 28.20 |
| 5 | 017 | 27.20 | 26.50 | 25.90 | 26.60 | 27.60 |
|   | 018 | 28.70 | 28.00 | 28.40 | 29.60 | 30.50 |
|   | 019 | 25.70 | 25.70 | 27.00 | 27.20 | 27.30 |
|   | 020 | 24.20 | 24.20 | 25.90 | 26.50 | 25.50 |
| 6 | 021 | 28.40 | 27.30 | 29.00 | 27.40 | 28.90 |
|   | 022 | 26.40 | 27.30 | 28.30 | 27.90 | 27.00 |
|   | 023 | 29.70 | 29.80 | 29.90 | 29.00 | 28.50 |
|   | 024 | 26.30 | 26.00 | 26.50 | 26.40 | 26.00 |
| 7 | 025 | 29.10 | 27.70 | 29.30 | 30.00 | 31.40 |
|   | 026 | 29.10 | 28.30 | 30.00 | 30.80 | 31.30 |
|   | 027 | 28.90 | 27.00 | 28.40 | 29.00 | 30.10 |
|   | 028 | 30.20 | 28.80 | 30.20 | 29.30 | 29.90 |
| 8 | 029 | 27.00 | 26.70 | 27.90 | 28.60 | 29.00 |
|   | 030 | 27.20 | 26.60 | 26.50 | 26.70 | 28.20 |
|   | 031 | 26.00 | 25.70 | 27.30 | 27.00 | 27.10 |
|   | 032 | 27.20 | 27.40 | 28.30 | 27.00 | 27.50 |
| 9 | 033 | 26.80 | 26.60 | 25.90 | 25.80 | 26.60 |
|   | 034 | 27.10 | 26.90 | 26.60 | 27.00 | 27.90 |
|   | 035 | 26.50 | 26.50 | 27.60 | 25.90 | 25.80 |
|   | 036 | 28.10 | 27.30 | 27.90 | 28.00 | 28.50 |
| 10 | 037 | 27.00 | 26.40 | 26.80 | 27.50 | 27.70 |
|   | 038 | 30.70 | 28.50 | 28.20 | 28.60 | 29.20 |
|   | 039 | 26.40 | 25.10 | 27.40 | 27.40 | 26.80 |
|   | 040 | 26.30 | 26.70 | 27.90 | 28.70 | 29.70 |

FIG. 8

Table 4: Body weights [%] in groups 1-10 on days 0 to 4

| Group | Animal ID | 03.06.2013 0 | 04.06.2013 1 | 05.06.2013 2 | 06.06.2013 3 | 07.06.2013 4 |
|---|---|---|---|---|---|---|
| 1 | 001 | 100.00% | 100.36% | 101.09% | 102.90% | 106.16% |
|   | 002 | 100.00% | 100.00% | 101.63% | 100.82% | 103.27% |
|   | 003 | 100.00% | 100.76% | 101.15% | 101.53% | 102.29% |
|   | 004 | 100.00% | 101.18% | 106.30% | 105.12% | 106.69% |
| 2 | 005 | 100.00% | 98.17% | 99.63% | 97.44% | 96.70% |
|   | 006 | 100.00% | 97.06% | 102.94% | 100.74% | 97.79% |
|   | 007 | 100.00% | 96.11% | 97.88% | 98.59% | 101.77% |
|   | 008 | 100.00% | 93.89% | 96.56% | 99.62% | 100.00% |
| 3 | 009 | 100.00% | 95.74% | 99.34% | 101.64% | 103.61% |
|   | 010 | 100.00% | 97.77% | 99.26% | 97.40% | 97.40% |
|   | 011 | 100.00% | 95.86% | 102.87% | 102.55% | 107.32% |
|   | 012 | 100.00% | 99.27% | 99.63% | 97.80% | 102.56% |
| 4 | 013 | 100.00% | 95.28% | 100.79% | 102.76% | 101.97% |
|   | 014 | 100.00% | 99.28% | 106.47% | 102.88% | 102.16% |
|   | 015 | 100.00% | 94.57% | 96.51% | 98.06% | 98.45% |
|   | 016 | 100.00% | 92.83% | 98.92% | 102.15% | 101.08% |
| 5 | 017 | 100.00% | 97.43% | 95.22% | 97.79% | 101.47% |
|   | 018 | 100.00% | 97.56% | 98.95% | 103.14% | 106.27% |
|   | 019 | 100.00% | 100.00% | 105.06% | 105.84% | 106.23% |
|   | 020 | 100.00% | 100.00% | 107.02% | 109.50% | 105.37% |
| 6 | 021 | 100.00% | 96.13% | 102.11% | 96.48% | 101.76% |
|   | 022 | 100.00% | 103.41% | 107.20% | 105.68% | 102.27% |
|   | 023 | 100.00% | 100.34% | 100.67% | 97.64% | 95.96% |
|   | 024 | 100.00% | 98.86% | 100.76% | 100.38% | 98.86% |
| 7 | 025 | 100.00% | 95.19% | 100.69% | 103.09% | 107.90% |
|   | 026 | 100.00% | 97.25% | 103.09% | 105.84% | 107.56% |
|   | 027 | 100.00% | 93.43% | 98.27% | 100.35% | 104.15% |
|   | 028 | 100.00% | 95.36% | 100.00% | 97.02% | 99.01% |
| 8 | 029 | 100.00% | 98.89% | 103.33% | 105.93% | 107.41% |
|   | 030 | 100.00% | 97.79% | 97.43% | 98.16% | 103.68% |
|   | 031 | 100.00% | 98.85% | 105.00% | 103.85% | 104.23% |
|   | 032 | 100.00% | 100.74% | 104.04% | 99.26% | 101.10% |
| 9 | 033 | 100.00% | 99.25% | 96.64% | 96.27% | 99.25% |
|   | 034 | 100.00% | 99.26% | 98.15% | 99.63% | 102.95% |
|   | 035 | 100.00% | 100.00% | 104.15% | 97.74% | 97.36% |
|   | 036 | 100.00% | 97.15% | 99.29% | 99.64% | 101.42% |
| 10 | 037 | 100.00% | 97.78% | 99.26% | 101.85% | 102.59% |
|   | 038 | 100.00% | 92.83% | 91.86% | 93.16% | 95.11% |
|   | 039 | 100.00% | 95.08% | 103.79% | 103.79% | 101.52% |
|   | 040 | 100.00% | 101.52% | 106.08% | 109.13% | 112.93% |

FIG. 9

Table 5: Results of necropsy

| Group | Animal no. | Day after treatment | Date of death | Termination criteria | Observation |
|---|---|---|---|---|---|
| Group 01: Vehicle | 1 | 4 | 07.06.2013 | SS | NAD |
| | 2 | 4 | 07.06.2013 | SS | NAD |
| | 3 | 4 | 07.06.2013 | SS | NAD |
| | 4 | 4 | 07.06.2013 | SS | NAD |
| Group 02: 4739 - 18mg/kg | 5 | 4 | 07.06.2013 | SS | nd |
| | 6 | 4 | 07.06.2013 | SS | nd |
| | 7 | 4 | 07.06.2013 | SS | nd |
| | 8 | 4 | 07.06.2013 | SS | nd |
| Group 03: 4739 - 35mg/kg | 9 | 4 | 07.06.2013 | SS | nd |
| | 10 | 4 | 07.06.2013 | SS | nd |
| | 11 | 4 | 07.06.2013 | SS | nd |
| | 12 | 4 | 07.06.2013 | SS | nd |
| Group 04: 4739 - 88mg/kg | 13 | 4 | 07.06.2013 | SS | NAD |
| | 14 | 4 | 07.06.2013 | SS | NAD |
| | 15 | 4 | 07.06.2013 | SS | NAD |
| | 16 | 4 | 07.06.2013 | SS | NAD |
| Group 05: 4813 - 19mg/kg | 17 | 4 | 07.06.2013 | SS | nd |
| | 18 | 4 | 07.06.2013 | SS | nd |
| | 19 | 4 | 07.06.2013 | SS | nd |
| | 20 | 4 | 07.06.2013 | SS | nd |
| Group 06: 4813 - 71mg/kg | 21 | 4 | 07.06.2013 | SS | nd |
| | 22 | 4 | 07.06.2013 | SS | nd |
| | 23 | 4 | 07.06.2013 | SS | nd |
| | 24 | 4 | 07.06.2013 | SS | nd |
| Group 07: 4813 - 141mg/kg | 25 | 4 | 07.06.2013 | SS | NAD |
| | 26 | 4 | 07.06.2013 | SS | NAD |
| | 27 | 4 | 07.06.2013 | SS | NAD |
| | 28 | 4 | 07.06.2013 | SS | NAD |
| Group 08: Reference compound - 13mg/kg | 29 | 4 | 07.06.2013 | SS | nd |
| | 30 | 4 | 07.06.2013 | SS | nd |
| | 31 | 4 | 07.06.2013 | SS | nd |
| | 32 | 4 | 07.06.2013 | SS | nd |
| Group 09: Reference compound - 55mg/kg | 33 | 4 | 07.06.2013 | SS | nd |
| | 34 | 4 | 07.06.2013 | SS | nd |
| | 35 | 4 | 07.06.2013 | SS | nd |
| | 36 | 4 | 07.06.2013 | SS | nd |
| Group 10: Reference compound - 133mg/kg | 37 | 4 | 07.06.2013 | SS | NAD |
| | 38 | 4 | 07.06.2013 | SS | NAD |
| | 39 | 4 | 07.06.2013 | SS | NAD |
| | 40 | 4 | 07.06.2013 | SS | NAD |

SS: Scheduled sacrificed
NAD: No abnormalities observed
nd: not determined

FIG. 10

RED-SHIFTED LUCIFERINS AND METHODS OF USING SAME

CROSS-REFERENCE TO RELATED APPLICATIONS

This application claims the benefit of priority to U.S. Provisional Application No. 61/777,208, filed Mar. 12, 2013, which is incorporated herein by reference in its entirety.

BACKGROUND

Bioluminescence with a longer-wavelength and lower-energy emission is of significant interest both for multiplexing applications with multiple emission colors and for in-depth tissue imaging where shorter wavelengths tend to be strongly absorbed. Many standard systems for optical imaging have limited utility in a whole-animal context due to the diminished transmission of light through biological samples. Light penetration is limited by the absorption coefficients of particular components in blood. Strong absorption by Hemoglobin (Hb) and oxygenated hemoglobin ($HbO_2$) diminish transmission (and penetration depth) of light through blood and animal tissues. Luminescent systems that emit light in the far red and near infrared region (680-900 nm) allow for optimal imaging due to a minimum in absorbance spectrums of Hb and $HbO_2$. This region of maximum light penetration is known as the whole animal "optical window". Bioluminescent reporter systems have been used extensively in research animals, yet still suffer from the limitations of diminished tissue penetration. Typical bioluminescent light emission wavelengths (460-620 nm) occur in a region with limited penetration depth. The ideal bioluminescent reporter systems in whole animals would benefit greatly from the bright light emission in the region of 680-900 nm. While numerous bioluminescent systems have been modified to shift visible light emission toward the red, none has achieved strong emission red enough to overlap significantly with the critical "optical window" of blood transmittance.

SUMMARY

In some embodiments, the invention provides a compound of formula to Formulas (Ia), (Ib) and (Ic):

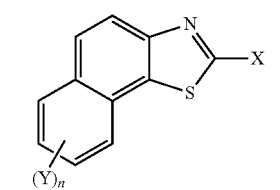
(Ia)

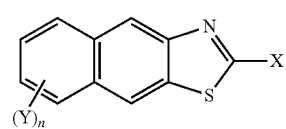
(Ib)

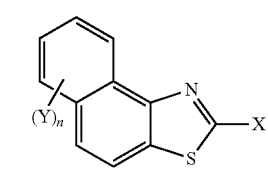
(Ic)

wherein
X is CN or

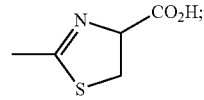

each Y is independently halo, $SO_3H$, $C_{1-4}$ alkyl, substituted $C_{1-4}$ alkyl, $OR^1$ or $NR^1R^2$;
each $R^1$ is H, $C_{1-10}$ alkyl or substituted $C_{1-10}$ alkyl;
each $R^2$ is H, $C_{1-10}$ alkyl or substituted $C_{1-10}$ alkyl; or
$R^1$ and $R^2$ together form a 4 to 8 membered ring;
n is 1 to 6;
two Y substituents may join together to form a ring containing from 5 to 7 ring atoms; and
wherein at least one Y is either OH or $NR^1R^2$.

In other embodiments, the invention provides a compound according to Formula (II):

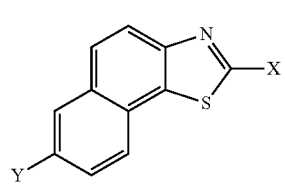
(II)

wherein
X is CN or

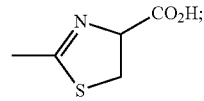

Y is $OR^1$ or $NR^1R^2$;
$R^1$ is H, $C_{1-10}$ alkyl or substituted $C_{1-10}$ alkyl; and
$R^2$ is H, $C_{1-10}$ alkyl or substituted $C_{1-10}$ alkyl; or
$R^1$ and $R^2$ together form a ring.

In yet other embodiments, the invention provides a compound according to Formula (III):

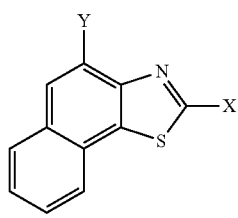
(III)

wherein
X is CN or

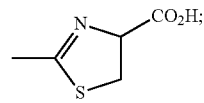

Y is OR¹ or NR¹R²;
R¹ is H, $C_{1-10}$ alkyl or substituted $C_{1-10}$ alkyl; and
R² is H, $C_{1-10}$ alkyl or substituted $C_{1-10}$ alkyl; or
R¹ and R² together form a ring.

In other embodiments, the invention provides a compound according to Formula (V):

(V)

wherein
X is CN or

Y is OR¹ or NR¹R²;
R¹ is H, $C_{1-10}$ alkyl or substituted $C_{1-10}$ alkyl; and
R² is H, $C_{1-10}$ alkyl or substituted $C_{1-10}$ alkyl; or
R¹ and R² together form a ring.

In yet other embodiments, the invention provides a compound according to Formula (VI):

(VI)

wherein
X is CN or

Y is OR¹ or NR¹R²;
R¹ is H, $C_{1-10}$ alkyl or substituted $C_{1-10}$ alkyl; and
R² is H, $C_{1-10}$ alkyl or substituted $C_{1-10}$ alkyl; or
R¹ and R² together form a ring.

In other embodiments, the invention provides a compound according to Formula (VII):

(VII)

wherein
X is CN or each Y is independently OR¹ or NR¹R²;
each R¹ is independently H, $C_{1-10}$ alkyl or substituted $C_{1-10}$ alkyl; and
each R² is independently H, $C_{1-10}$ alkyl or substituted $C_{1-10}$ alkyl; or
R¹ and R² together form a ring.

In yet other embodiments, the invention provides a compound according to Formula (IX):

(IX)

wherein
X is CN or

Y is OR;
R is

W is S, $NR_N$, or O;
Z is S, $NR_N$, O or CH; and
$R_N$ is H, $C_{1-4}$ alkyl, or substituted $C_{1-4}$ alkyl.

In other embodiments, the invention provides a compound according to Formula (X):

(X)

wherein
X is CN or

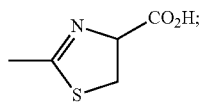

Y is OR$^1$ or NR$^1$R$^2$; and
R$^1$ is H, C$_{1-10}$ alkyl or substituted C$_{1-10}$ alkyl;
R$^2$ is H, C$_{1-10}$ alkyl or substituted C$_{1-10}$ alkyl; or
R$^1$ and R$^2$ together form a 4 to 8 membered ring.

In other embodiments, the invention provides a compound according to Formula (XI):

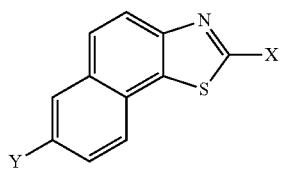

(XI)

wherein
X is CN or

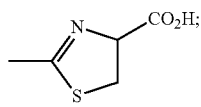

Y is OR; and
R is

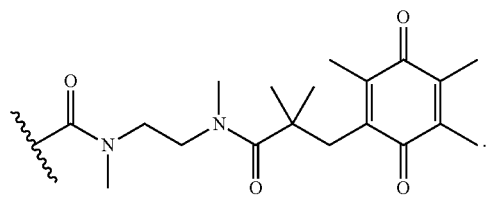 [SMILES: *C(=O)N(C)CCN(C)C(=O)C(C)(C)CC1=C(C)C(=O)C(C)=C(C)C1=O]

In other embodiments, the invention provides a compound according to Formula (XII):

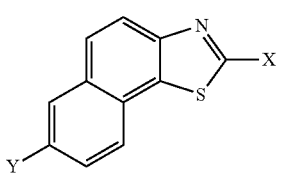

(XII)

wherein
X is CN or

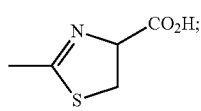

Y is OR;
R is

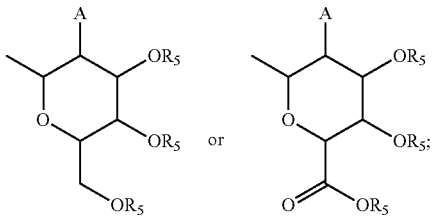

A is OR or NHAc;
each R$_5$ is independently H, a monosaccharide or a polyethylene glycol moiety of up to 40 units.

In yet other embodiments, the invention provides a compound according to Formula (XIII):

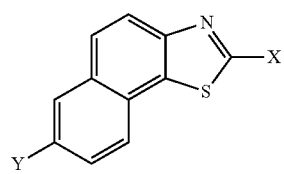

(XIII)

wherein
X is CN or

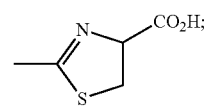

Y is NHR;
R is

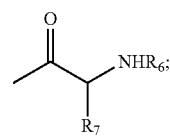

R$_7$ is an amino acid side chain;
R$_6$ is H, a nitrogen protecting group, or a chain of up to 35 amino acids.

In yet other embodiments, the invention provides a compound according to Formula (XIV):

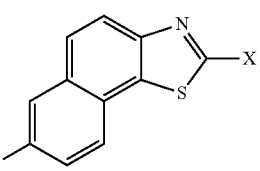

(XIV)

wherein
X is —CH(OR$_{10}$)$_2$;
R$_{10}$ is C$_{1-4}$ alkyl, substituted C$_{1-4}$ alkyl, benzyl, or substituted benzyl;
Y is OR$^1$ or NR$^1$R$^2$; and
R$^1$ is H, C$_{1-10}$ alkyl or substituted C$_{1-10}$ alkyl;
R$^2$ is H, C$_{1-10}$ alkyl or substituted C$_{1-10}$ alkyl; or
R$^1$ and R$^2$ together form a 4 to 8 membered ring.

In other embodiments, the invention provides a compound according to Formula (XV):

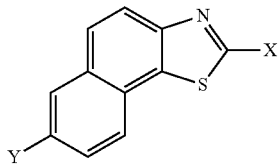
(XV)

wherein
X is CN or

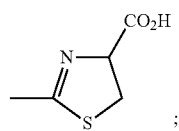
;

Y is H or OR; and
R is C$_{1-10}$ alkyl, substituted C$_{1-10}$ alkylaryl, substituted aryl, aralkyl or substituted aralkyl.

In other embodiments, the invention provides a compound according to Formula (XVI):

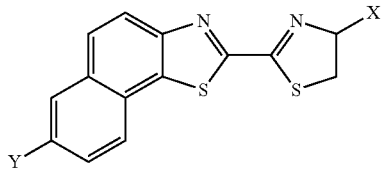
(XVI)

wherein
X is —CH(OR$_{10}$)$_2$;
R$_{10}$ is C$_{1-4}$ alkyl, substituted C$_{1-4}$ alkyl, benzyl or substituted benzyl;
Y is OR$^1$ or NR$^1$R$^2$; and
R$^1$ is H, C$_{1-10}$ alkyl or substituted C$_{1-10}$ alkyl;
R$^2$ is H, C$_{1-10}$ alkyl or substituted C$_{1-10}$ alkyl; or
R$^1$ and R$^2$ together form a 4 to 8 membered ring.

In other embodiments, the invention provides a compound according to Formula (XVII):

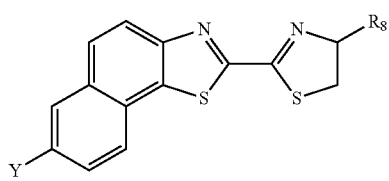
(XVII)

wherein
R$_8$ is CH$_2$OH, C(O)R$_{10}$ or —C(O)ZR$_9$;
Z is O or NH;
R$_9$ is C$_{1-7}$ alkyl or substituted C$_{1-7}$ alkyl;
R$_{10}$ is a peptide;
Y is OR$^1$ or NR$^1$R$^2$; and
R$^1$ is H, C$_{1-10}$ alkyl or substituted C$_{1-10}$ alkyl;
R$^2$ is H, C$_{1-10}$ alkyl or substituted C$_{1-10}$ alkyl; or
R$^1$ and R$^2$ together form a 4 to 8 membered ring.

In yet other embodiments, the invention provides a compound according to Formula (XVIII):

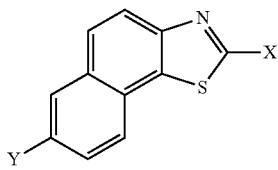
(XVIII)

wherein
X is CN or

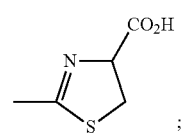
;

Y is OR;
R is

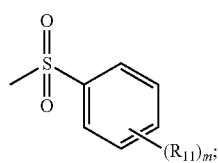

each R$_{11}$ is independently H, C$_{1-6}$ alkyl, substituted C$_{1-6}$ alkyl, CF$_3$, halogen, NO$_2$, CO$_2$R$_{12}$ or any two adjacent R$_{11}$ can form a fused ring provided that at least one of R$_{11}$ is NO$_2$; and
R$_{12}$ is H, C$_{1-6}$ alkyl or substituted C$_{1-6}$ alkyl.

In other embodiments, the invention provides a compound according to Formula (XIX):

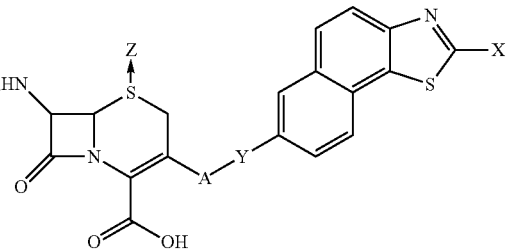
(XIX)

wherein
X is CN or

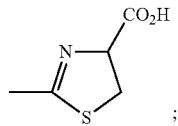

Y is O, NH, N(C$_{1-7}$ alkyl), or N (substituted C$_{1-7}$ alkyl);
Z is absent or O;
A is C$_{1-4}$ alkylene or substituted C$_{1-4}$ alkylene; and
R$_{14}$ is H, phenacetyl, or a cephalosporin side chain.

In other embodiments, the invention provides a compound according to Formula (XX):

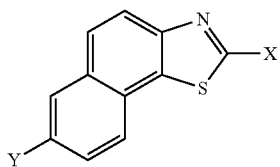

(XX)

wherein
X is CN or

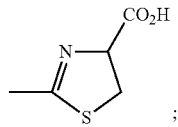

Y is L-R;
L is a linker; and
R is a boronic acid or borate ester.

In other embodiments, the invention provides a method for detecting luminescence in a sample comprising contacting a sample with a compound according to the present invention; contacting the sample with a luciferase, if it is not present in the sample; and detecting luminescence.

In yet other embodiments, the invention provides A method for detecting luminescence in a transgenic animal comprising administering a compound according to the present invention to a transgenic animal; and detecting luminescence; wherein the transgenic animal expresses a luciferase.

In other embodiments, the invention provides a method of detecting the presence or amount of a non-luciferase enzyme comprising contacting a sample suspected of containing the enzyme with a compound according to the invention; adding a luciferase reaction mixture to the sample; and detecting luminescence of the sample.

In other embodiments, the invention provides a method of detecting the presence of a non-luciferase enzyme in vivo comprising administering a compound according to the invention to a transgenic animal and detecting luminescence; wherein the transgenic animal expresses luciferase.

In yet other embodiments, the invention provides a method of detecting the presence of a non-luciferase enzyme comprising administering a compound according to the invention to an animal; obtaining a sample from the animal; adding a luciferase reaction mixture to the sample; and detecting luminescence of the sample.

In other embodiments, the invention provides an in vitro method of screening for modulators of a non-luciferase enzyme comprising contacting cells with a test compound; adding a compound according to any one of claims 22-33 to form a mixture; adding a luciferase reaction mixture to the mixture; and detecting luminescence.

In other embodiments, the invention provides a kit comprising a compound according to the invention.

Other aspects of the invention will become apparent by consideration of the detailed description and accompanying drawings.

BRIEF DESCRIPTION OF THE DRAWINGS

FIG. 4A shows the luminescence (RLUs), and FIG. 4B shows the fold luminescence over background.

FIG. 6 shows data from clinical signs and animal behavior after a single dose of PBI-4739 or PBI-4813 in female CD-1 mice.

FIG. 7 shows the survival rate after a single dose of PBI-4739 or PBI-4813 in female CD-1 mice.

FIG. 8 shows body weights in grams after a single dose of PBI-4739 or PBI-4813 in female CD-1 mice.

FIG. 9 shows body weights in percentages after a single dose of PBI-4739 or PBI-4813 in female CD-1 mice.

FIG. 10 shows necropsy results after a single dose of PBI-4739 or PBI-4813 in female CD-1 mice.

DETAILED DESCRIPTION

Figure 1:
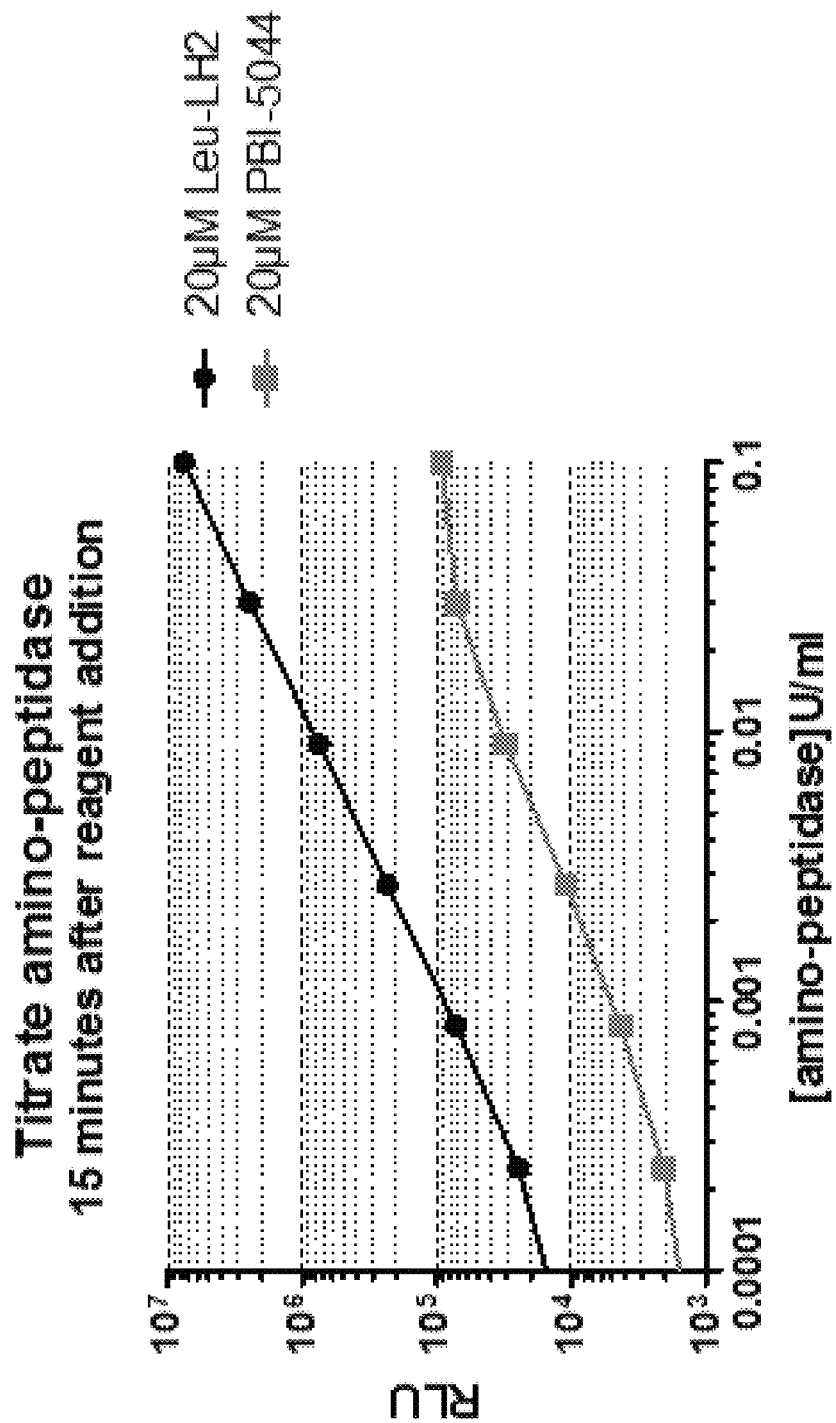
FIG. 1 illustrates the bioluminescent response of leucine adducts of aminoluciferin control (Leu-luciferin; black circles) or aminoisonaphtholuciferin (PBI-5044; gray squares) as a function of added aminopeptidase.

Before any embodiments of the invention are explained in detail, it is to be understood that the invention is not limited in its application to the details of construction, and the arrangement of components set forth in the following description or illustrated in the following drawings. The invention is capable of other embodiments and of being practiced or of being carried out in various ways.

DEFINITIONS

As used herein, the following terms and expressions have the indicated meanings. It will be appreciated that the compounds of the present invention contain asymmetrically substituted carbon atoms and may be isolated in optically active or racemic forms. It is well known in the art how to prepare optically active forms such as by resolution of racemic forms or by synthesis from optically active starting materials. All chiral, diastereomeric, racemic forms and all geometric isomeric forms of a structure are part of this invention.

Specific values listed below for radicals, substituents and ranges are for illustration only; they do not exclude other defined values or other values within defined ranges for the radicals and substituents.

As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano. Additionally, the suitable indicated groups can include, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, NO$_2$, =N$_2$, —N$_3$, NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=O)(O)$_2$, —P(=O)(OH)$_2$, —C(=O)R, —C(=O)X, —C(S)R, —C(O)OR, —C(O)O, —C(S)OR, —C(O)SR, —C(S)SR, —C(O)NRR, —C(S) NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is oxo (=O) or thioxo (=S), or the like, then two hydrogen atoms on the substituted atom are replaced.

As used herein, the term "alkyl" refers to a branched, unbranched, or cyclic hydrocarbon having, for example, from 1 to 30 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

The term "alkenyl" refers to a monoradical branched or unbranched partially unsaturated hydrocarbon chain (i.e. a carbon-carbon, sp$^2$ double bond). In some embodiments, an alkenyl group can have from 2 to 10 carbon atoms, or 2 to 6 carbon atoms. In other embodiments, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In some embodiments, the alkynyl group can have from 2 to 10 carbon atoms, or 2 to 6 carbon atoms. In other embodiments, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In some embodiments, alkoxy groups include, e.g., methoxy, ethoxy, n-propoxy, isopropoxy, n-butoxy, tert-butoxy, sec-butoxy, n-pentoxy, n-hexoxy, 1,2-dimethylbutoxy, and the like. The alkoxy can be unsubstituted or substituted.

As used herein, "aryl" or "Ar" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 30 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In some embodiments, the haloalkyl can be substituted with 1, 2, 3, 4, or 5 halo groups. In other embodiments, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2-20 carbon atoms in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In some embodiments, the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In other embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* 1960, 82, 5566. In some embodiments, "heterocycle" includes a "carbocycle" as defined herein, wherein one or more (e.g. 1, 2, 3, or 4) carbon atoms have been replaced with a heteroatom (e.g. O, N, or S).

Examples of heterocycles, by way of example and not limitation, include, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or 3-carboline. In some embodiments, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "amino" refers to —NH$_2$. The amino group can be optionally substituted as defined herein for the term "substituted".

The term "alkylamino" refers to —NR$_2$, wherein at least one R is alkyl and the second R is alkyl or hydrogen.

The term "acylamino" refers to N(R)C(=O)R, wherein each R is independently hydrogen, alkyl, or aryl.

The term "hydroxyalkyl" refers to an alkyl group substituted by —OH.

The term "alkylcarboxylic acid" refers to an alkyl group substituted by —COOH.

The term "amino acid" includes a residue of a natural amino acid in D or L form as well as unnatural amino acids (e.g. beta-alanine, phosphoserine, phosphothreonine, phosphotyrosine, hydroxyproline, gamma-carboxyglutamate, hippuric acid, octahydroindole-2-carboxylic acid, statine, 1,2,3,4-tetrahydroisoquinoline-3-carboxylic acid, penicillamine, ornithine, citrulline, alpha-methylalanine, para-benzolylphenylalanine, phenylglycine, propargylglycine, sacrosine, and tert-butylglycine). The term also comprises natural and unnatural amino acids bearing a conventional amino protecting group (e.g. acetyl or benzoylcarboyl), as well as natural and unnatural amino acids protected at the carboxy terminus (e.g. as ($C_{1-6}$ alkyl, phenyl or benzyl ester or amide; or as an alpha-methylbenzyl amide). Other suitable amino and carboxy protecting groups are known to those skilled in the art. (See, e.g., Greene, T. W.; Wutz, P. G. M. *Protecting Groups in Organic Synthesis*, $2^{nd}$ edition, John Wiley & Sons, Inc., New York (1991) and references cited therein). An amino acid side chain may also include a side chain containing a known modification such as acetylated, mono-, di- or tri-fluoroacetylated or 1-3× methylated lysine, methylated arg (mono, symmetrical bis, asymmetrical bis), phosphorylated Ser, Thr or Tyr, fatty acylation e.g. myristoylation, glycosylation, etc.

The term "amino acid side chain" refers to any amino acid side chain, whether natural or synthetic, found in an "amino acid" as defined above. This includes, but is not limited to, the twenty standard occurring side chains.

The term "peptide" refers to a sequence of 2 to 35 amino acids or peptidyl residues. The sequence may be linear or cyclic. For example, a cyclic peptide may result from an appropriate amide or ester linkage or from disulfide formation between two cysteine residues in a sequence. Suitably, a peptide comprises 3 to 20 or 5 to 15 amino acids. Peptide sequences specifically recited herein are written with the amino terminus on the left and the carboxy terminus on the right.

The term "interrupted" indicates that another group is inserted between two adjacent carbon atoms (and the hydrogen atoms to which they are attached (e.g., methyl ($CH_3$), methylene ($CH_2$) or methine (CH))) of a particular carbon chain being referred to in the expression using the term "interrupted, provided that each of the indicated atoms' normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl ($SO_2$). Alkyl groups can be interrupted by one ore more (e.g., 1, 2, 3, 4, 5, or about 6) of the aforementioned suitable groups. The site of interruption can also be between a carbon atom of an alkyl group and a carbon atom to which the alkyl group is attached.

The term "luciferase" unless specified otherwise, refers to a naturally occurring, recombinant or mutant luciferase. The luciferase, if naturally occurring, may be obtained easily by the skilled person from an organism. If the luciferase is one that occurs naturally or is a recombinant or mutant luciferase, i.e. one which retains activity in a luciferase-luciferin reaction of a naturally occurring luciferase, it can be obtained readily from a culture of bacteria, yeast, mammalian cells, insect cells, plant cells, or the like, transformed to express a nucleic acid encoding the luciferase. Further, the recombinant or mutant luciferase can be derived from an in vitro cell-free system using a nucleic acid encoding the luciferase. Luciferases are available from Promega Corporation, Madison, Wis.

As used herein, "bioluminescence" or "luminescence" is light produced as a result of a reaction between an enzyme and a substrate that generates light. Examples of such enzymes (bioluminescent enzymes) include firefly luciferase, e.g. *Photinus pyralis* or *Photinus pennslyvanica*, click beetle luciferase, cypridina luciferase, and the like.

A "luciferase reaction mixture" contains a luciferase enzyme and materials that will allow the luciferase enzyme to generate a light signal. The materials needed, and the particular concentrations and/or amounts, of the materials needed to generate a luminescent signal will vary depending on the luciferase enzyme used as well as the type of luciferase-based assay being performed. In general, for firefly luciferase, these materials can include: ATP, magnesium ($Mg^{2+}$) salt, such as magnesium sulfate, a firefly luciferase enzyme, e.g., a thermostable firefly luciferase, and a luciferin capable of generating light when the luciferin is used as a substrate for the firefly luciferase. Often other materials will be added to the solution including: a buffer to maintain the reaction at the proper pH, an additive such as PRIONEX or Bovine serum albumin (BSA) to help maintain luciferase activity, reducing agents, detergents, esterases, salts, amino acids, e.g. D-cysteine, etc. An example luciferase reaction mixture would contain a thermostable firefly luciferase, $MgSO_4$, ATP, Tergitol NP-9, and Tricine. An alternative example luciferase reaction mixture would include Oplophorus luciferase, e.g., NanoLuc luciferase, buffer, e.g., Tris-Cl or Tris base, and optionally a background reduction agent, e.g., TCEP.

Compounds

The present invention provides a compound according to Formulas (Ia), (Ib) and (Ic):

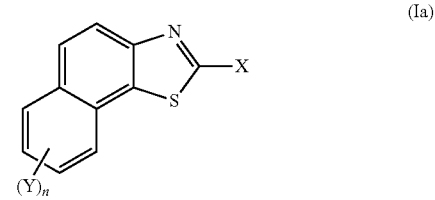

(Ia)

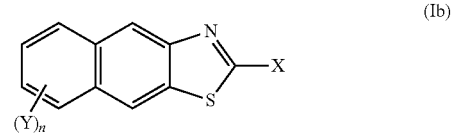

(Ib)

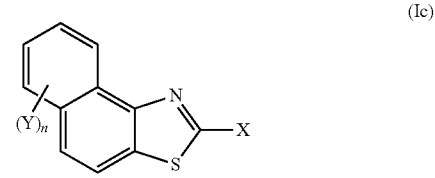

(Ic)

wherein
X is CN or

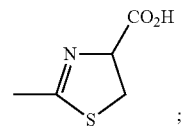

;

each Y is independently halo, $SO_3H$, $C_{1-4}$ alkyl, substituted $C_{1-4}$ alkyl, $OR^1$ or $NR^1R^2$;

each $R^1$ is H, $C_{1-10}$ alkyl or substituted $C_{1-10}$ alkyl;

each $R^2$ is H, $C_{1-10}$ alkyl or substituted $C_{1-10}$ alkyl; or $R^1$ and $R^2$ together form a 4 to 8 membered ring;

n is 1 to 6;

two Y substituents may join together to form a ring containing from 5 to 7 ring atoms; and wherein at least one Y is either OH or $NR^1R^2$.

Compounds according to the present invention include, but are not limited to:

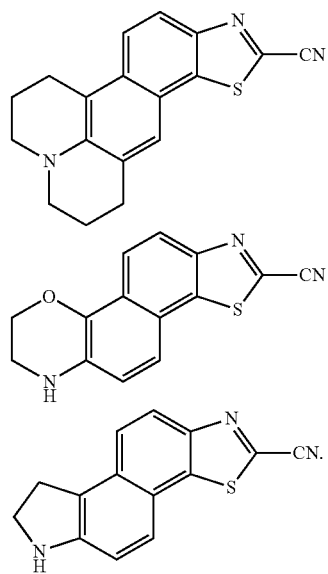

In other embodiments, the invention provides a compound according to Formula (II):

(II)

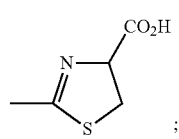

wherein
  X is CN or

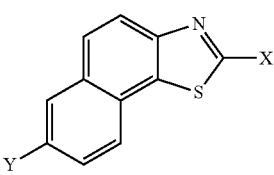

Y is $OR^1$ or $NR^1R^2$;
$R^1$ is H, $C_{1-10}$ alkyl or substituted $C_{1-10}$ alkyl; and
$R^2$ is H, $C_{1-10}$ alkyl or substituted $C_{1-10}$ alkyl; or
$R^1$ and $R^2$ together form a ring.

In a further embodiments, the invention provides a compound according to Formula (III):

(III)

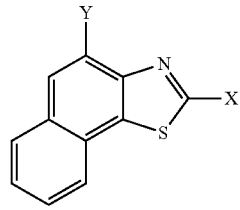

wherein
  X is CN or

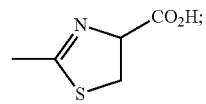

Y is $OR^1$ or $NR^1R^2$;
$R^1$ is H, $C_{1-10}$ alkyl or substituted $C_{1-10}$ alkyl; and
$R^2$ is H, $C_{1-10}$ alkyl or substituted $C_{1-10}$ alkyl; or
$R^1$ and $R^2$ together form a ring.

In yet other embodiments, the invention provides a compound according to Formula (IV):

(IV)

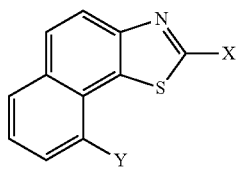

wherein
  X is CN or

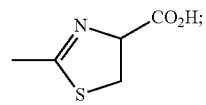

Y is $OR^1$ or $NR^1R^2$;
$R^1$ is H, $C_{1-10}$ alkyl or substituted $C_{1-10}$ alkyl; and
$R^2$ is H, $C_{1-10}$ alkyl or substituted $C_{1-10}$ alkyl; or
$R^1$ and $R^2$ together form a ring.

In other embodiments, the invention provides a compound according to Formula (V):

(V)

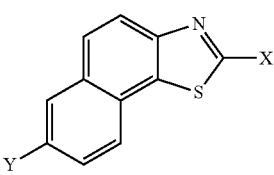

wherein
X is CN or

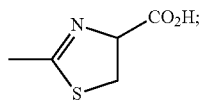

Y is OR¹ or NR¹R²;
R¹ is H, $C_{1-10}$ alkyl or substituted $C_{1-10}$ alkyl; and
R² is H, $C_{1-10}$ alkyl or substituted $C_{1-10}$ alkyl; or
R¹ and R² together form a ring.

In other embodiments, the invention provides a compound according to Formula (VI):

(VI)

wherein
X is CN or

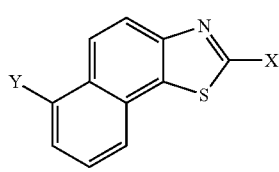

Y is OR¹ or NR¹R²;
R¹ is H, $C_{1-10}$ alkyl or substituted $C_{1-10}$ alkyl; and
R² is H, $C_{1-10}$ alkyl or substituted $C_{1-10}$ alkyl; or
R¹ and R² together form a ring.

In an additional embodiments, the invention provides a compound according to Formula (VII):

(VII)

wherein
X is CN or each Y is independently OR¹ or NR¹R²;
each R¹ is independently H, $C_{1-10}$ alkyl or substituted $C_{1-10}$ alkyl; and
each R² is independently H, $C_{1-10}$ alkyl or substituted $C_{1-10}$ alkyl; or
R¹ and R² together form a ring.

In certain embodiments, the emission maximum of the compounds according to the present invention is at least about 650 nm, about 655 nm, about 680, or about 760 nm. nm.

Pro-Substrates

The present invention also provides compounds which are substrates for various non-luciferase enzymes and are pro-substrates for luciferase enzymes. The non-luciferase enzymes include, but are not limited to, reductases, glycosidases, proteases, peptidases, oxidases, esterases, cytochrome P450s, beta-lactamases, glycosylases and glutathione transferases.

In some embodiments, these pro-substrates have a substituent that is a substrate for a non-luciferase position at the one or more Y positions which is cleaved to form (VIII)

wherein
X is CN or each Y is OH or $NH_2$; and
n is 1 to 3.

Reductase Substrates

In some embodiments, the compound is a reductase substrate. In some embodiments, a reductase substrate has the formula:

(IX)

wherein
X is CN or

Y is OR;
R is

W is S, $NR_N$, or O;

Z is S, $NR_N$, O or CH; and $R_N$ is H, $C_{1-4}$ alkyl, or substituted $C_{1-4}$ alkyl.

In some embodiments, a reductase substrate has the formula:

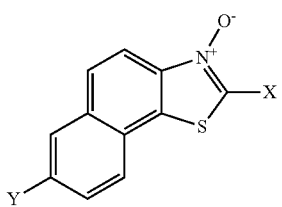

(X)

wherein

X is CN or

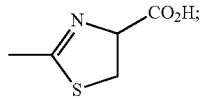

Y is $OR^1$ or $NR^1R^2$; and $R^1$ is H, $C_{1-10}$ alkyl or substituted $C_{1-10}$ alkyl;

$R^2$ is H, $C_{1-10}$ alkyl or substituted $C_{1-10}$ alkyl; or $R^1$ and $R^2$ together form a 4 to 8 membered ring.

In some embodiments, a reductase substrate has the formula:

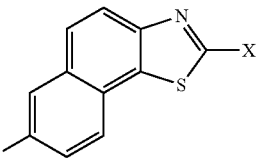

(XI)

wherein

X is CN or

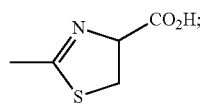

Y is OR; and

R is

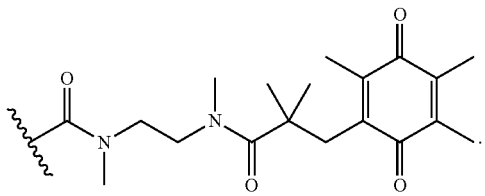 [SMILES: *C(=O)N(C)CCN(C)C(=O)C(C)(C)CC1=C(C)C(=O)C(C)=C(C)C1=O]

Reductase substrates include, but are not limited to, the following compounds:

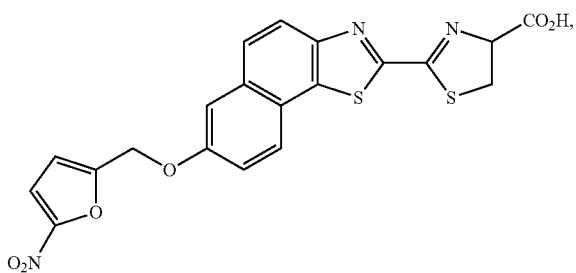

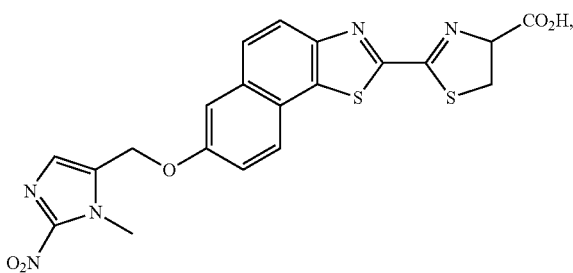

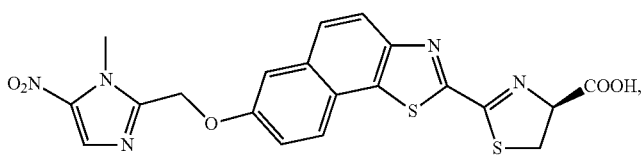

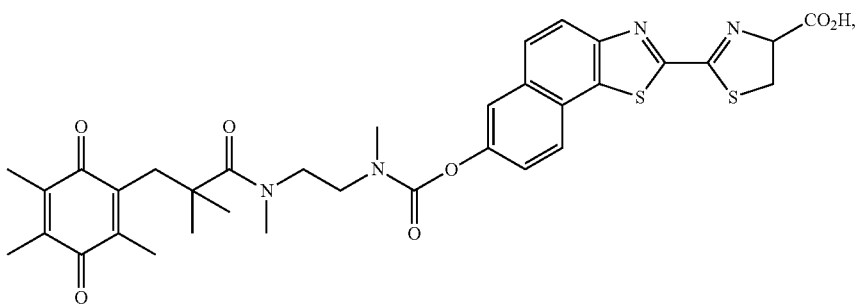

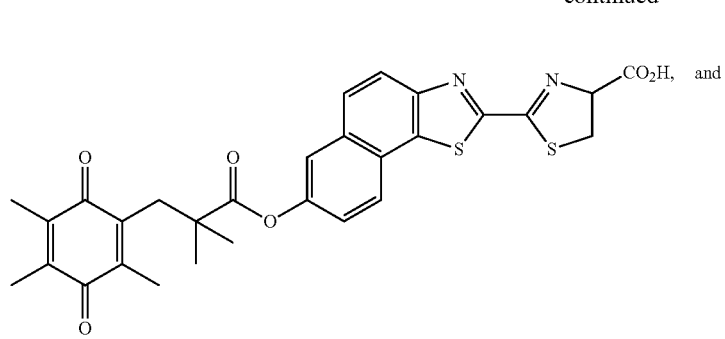 and 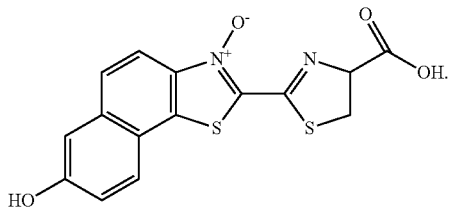

Glycosidase Substrates

In some embodiments, the compound is a glycosidase substrate. In some embodiments, the glycosidase substrate is a compound of formula:

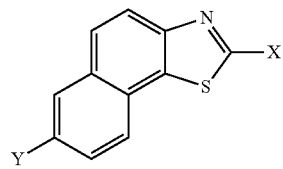 (XII)

wherein
X is CN or

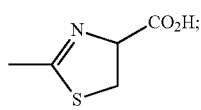

Y is OR;
R is

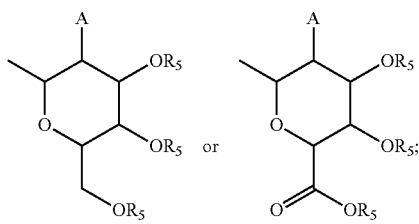

A is OR or NHAc;
each $R_5$ is independently H, a monosaccharide or a polyethylene glycol moiety of up to 40 units.

Glycosidase substrates include, but are not limited to, the following compounds:

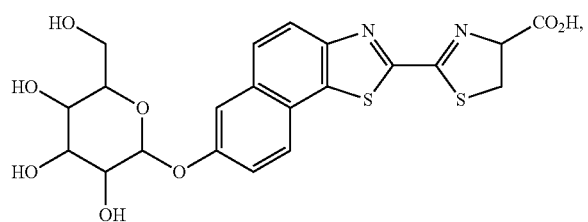

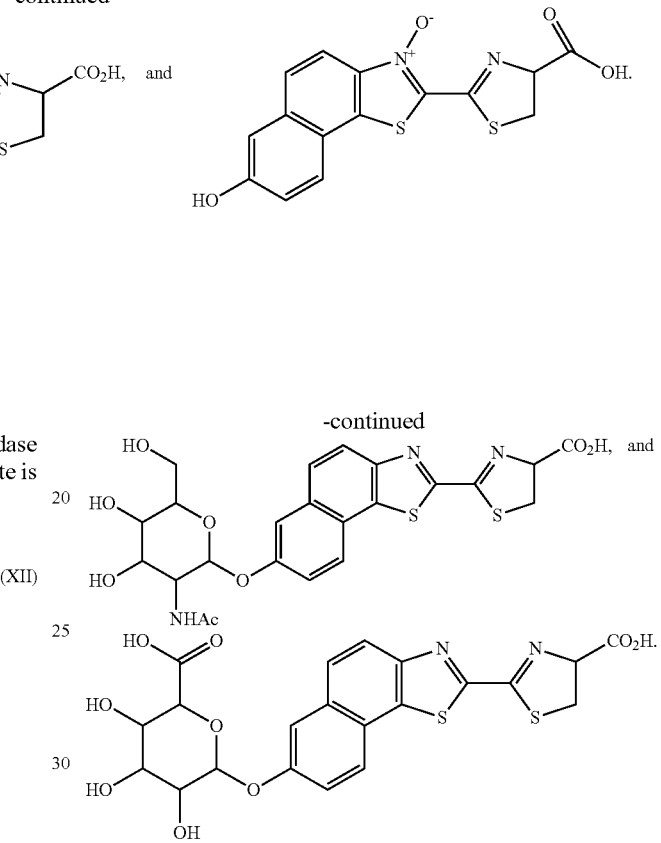

Protease and Protease-Dependent Protein Modifying Substrates

In some embodiments, the compound is a protease or protease-dependent protein modifying substrate. In some embodiments, the substrate is a compound of formula:

 (XIII)

wherein
X is CN or

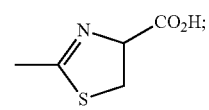

Y is NHR;
R is

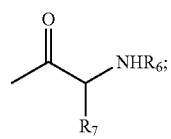

$R_7$ is an amino acid side chain;

$R_6$ is H, a nitrogen protecting group, or a chain of up to 20 amino acids.

Suitable nitrogen protecting groups include, but are not limited to, those traditionally known to those skilled in the art, such as Boc, Cbz, Ac and Fmoc.

These substrates include, but are not limited to, the following compounds:

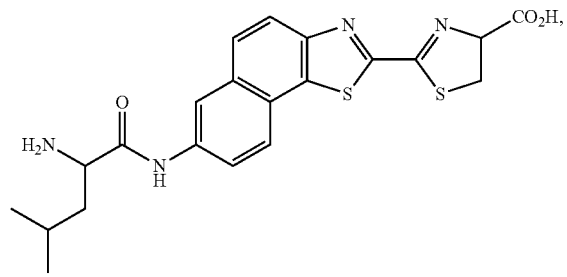

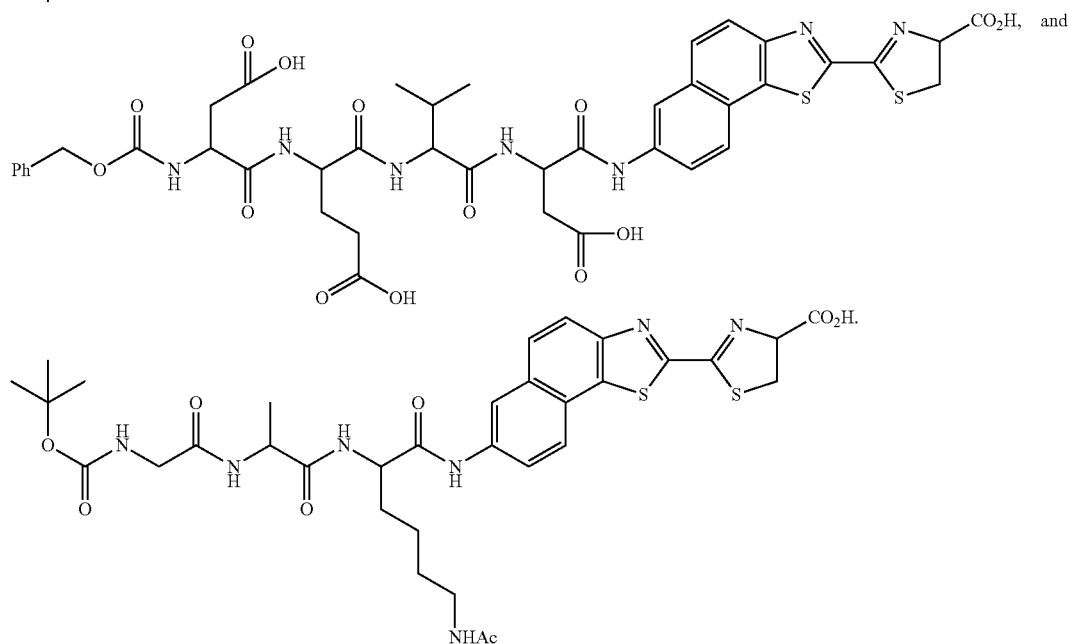

Oxidase Substrates

In some embodiments, the compound is an oxidase substrate. In some embodiments, an oxidase substrate is a compound of formula:

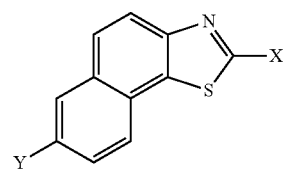

(XIV)

wherein

X is —CH(OR$_{10}$)$_2$;

R$_{10}$ is C$_{1-4}$ alkyl, substituted C$_{1-4}$ alkyl, benzyl, or substituted benzyl;

Y is OR$^1$ or NR$^1$R$^2$; and

R$^1$ is H, C$_{1-10}$ alkyl or substituted C$_{1-10}$ alkyl;

R$^2$ is H, C$_{1-10}$ alkyl or substituted C$_{1-10}$ alkyl; or

R$^1$ and R$^2$ together form a 4 to 8 membered ring.

In some embodiments, an oxidase substrate is a compound of formula:

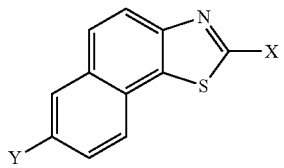

(XV)

wherein

X is CN or

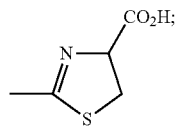

Y is H or OR; and

R is $C_{1-10}$ alkyl, substituted $C_{1-10}$ alkyl, aryl, substituted aryl, aralkyl or substituted aralkyl.

In some embodiments, an oxidase substrate is a compound of formula:

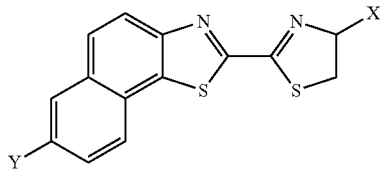

(XVI)

wherein

X is —CH(OR$_{10}$)$_2$;

R$_{10}$ is $C_{1-4}$ alkyl, substituted $C_{1-4}$ alkyl, benzyl or substituted benzyl;

Y is OR$^1$ or NR$^1$R$^2$; and

R$^1$ is H, $C_{1-10}$ alkyl or substituted $C_{1-10}$ alkyl;

R$^2$ is H, $C_{1-10}$ alkyl or substituted $C_{1-10}$ alkyl; or

R$^1$ and R$^2$ together form a 4 to 8 membered ring.

Oxidase substrates include, but are not limited to, the following compounds:

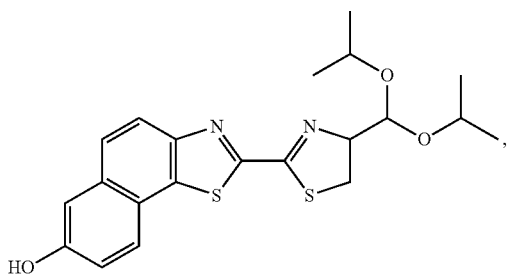

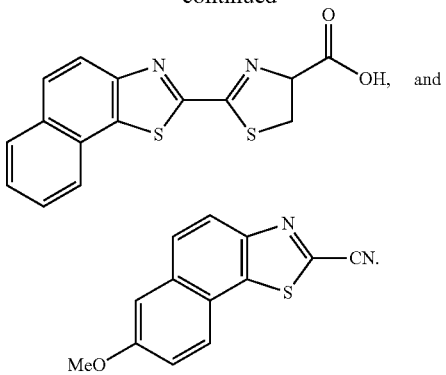

Carboxyl-Based Pro-Substrates

In some embodiments, the compound is a carboxyl-based pro-substrate. In some embodiments, the carboxyl-based pro-substrate is a compound of formula:

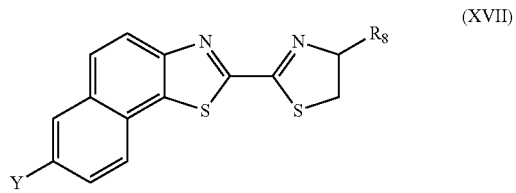

(XVII)

wherein

R$_8$ is CH$_2$OH, C(O)R$_{10}$ or —C(O)ZR$_9$;

Z is O or NH;

R$_9$ is $C_{1-7}$ alkyl or substituted $C_{1-7}$ alkyl;

R$_{10}$ is a peptide;

Y is OR$^1$ or NR$^1$R$^2$; and

R$^1$ is H, $C_{1-10}$ alkyl or substituted $C_{1-10}$ alkyl;

R$^2$ is H, $C_{1-10}$ alkyl or substituted $C_{1-10}$ alkyl; or

R$^1$ and R$^2$ together form a 4 to 8 membered ring.

Carboxyl-based pro-substrates include, but are not limited to, the following compounds:

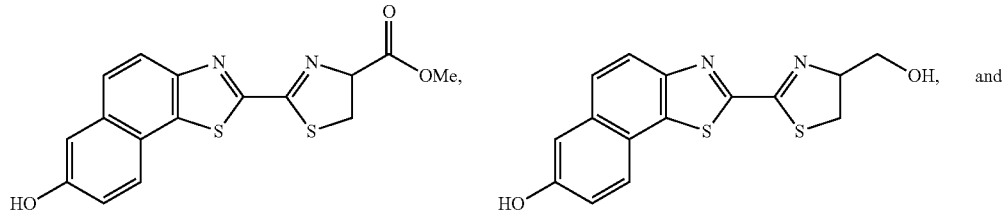

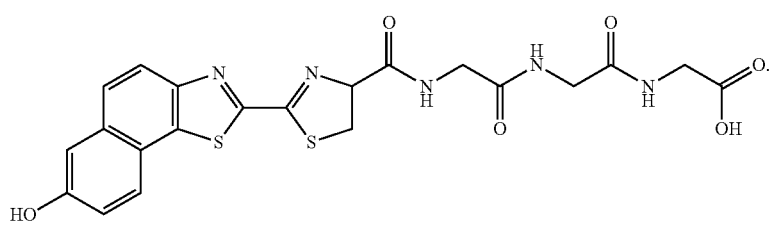

Glutathione Transferase Substrate

In some embodiments, the compound may be a glutathione transferase substrate. In some embodiments, the glutathione transferase substrate is a compound of formula:

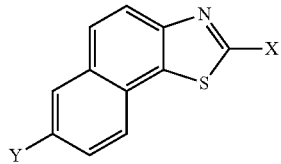

(XVIII)

wherein
X is CN or

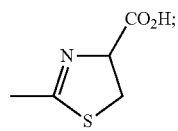

Y is OR;
R is

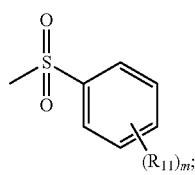

each $R_{11}$ is independently H, $C_{1-6}$ alkyl, substituted $C_{1-6}$ alkyl, $CF_3$, halogen, $NO_2$, $CO_2R_{12}$ or any two adjacent $R_{11}$ can form a fused ring provided that at least one of $R_{11}$ is $NO_2$; and
$R_{12}$ is H, $C_{1-6}$ alkyl or substituted $C_{1-6}$ alkyl.

Glutathione transferase substrates include, but are not limited to, the following compounds:

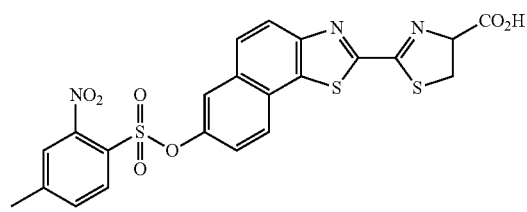

and

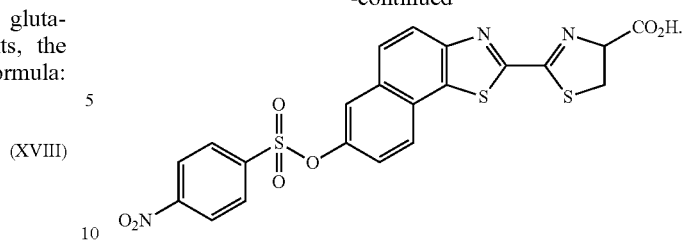

Beta-Lactamase Substrates

In some embodiments, the compound is a beta-lactamase substrate. In some embodiments, the beta-lactamase substrate is a compound of formula:

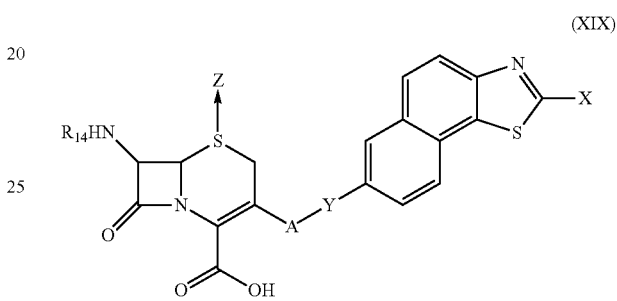

(XIX)

wherein
X is CN or

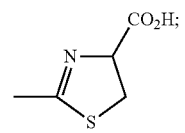

Y is O, NH, N($C_{1-7}$ alkyl), or N (substituted $C_{1-7}$ alkyl);
Z is absent or O;
A is $C_{1-4}$ alkylene or substituted $C_{1-4}$ alkylene; and
$R_{14}$ is H, phenacetyl, or a cephalosporin side chain.

Suitable cephalosporin side chains include those known to one of ordinary skill in the art.

Beta-lactamase substrates include, but are not limited to, the following compounds:

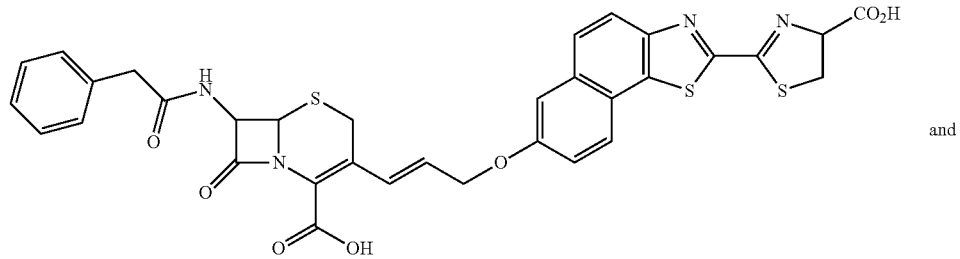

and

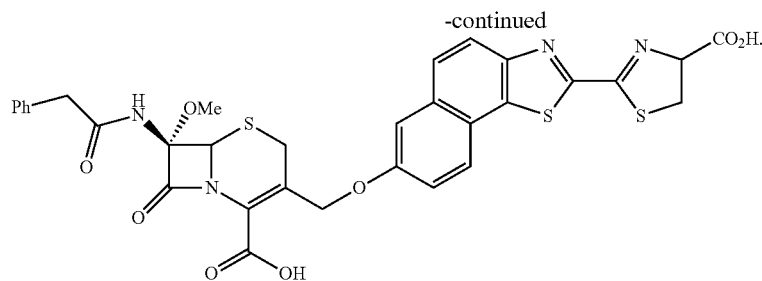

Other Pro-Substrates

The present invention also provides compounds which react with various biologically important small molecules, such as hydrogen peroxide, and are pro-substrates for luciferase enzymes. In some embodiments, these compounds are reactive to hydrogen peroxide. In some embodiments, these compounds have the formula:

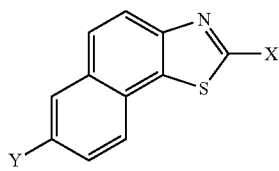
(XX)

wherein

X is CN or

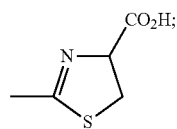

Y is L-R;

L is a linker; and

R is a boronic acid or borate ester.

In some embodiments, R is —B(OR$_{15}$)$_2$; wherein each R$_{15}$ is independently selected from H and C$_{1-4}$ alkyl. In some embodiments, R is

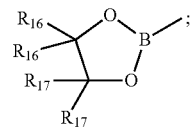

wherein each R$_{16}$ and R$_{17}$ is independently selected from H, C$_{1-4}$ alkyl, substituted C$_{1-4}$ alkyl, CF$_3$, phenyl or substituted phenyl; or R$_{16}$ and R$_{17}$ together can be an alkyl ring having from 3-7 carbons or can be replaced by a fused 6-membered aromatic ring.

In some embodiments, the linker is a direct bond. In other embodiments, the linker is

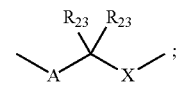

wherein

A is —C$_6$(R$_{20}$)$_4$—, —O—C$_6$(R$_{20}$)$_4$— or —(CR$_{21}$=CR$_{21}$)$_n$— or —S—C$_6$(R$_{20}$)$_4$— or —NR'—C$_6$(R$_{20}$)$_4$ or a direct bond;

R' is H, C$_{1-4}$ alkyl, or substituted C$_{1-4}$ alkyl;

each R$_{23}$ is independently halo, H, C$_{1-4}$ alkyl, substituted C$_{1-4}$ alkyl, C$_{1-4}$ hydroxyalkyl, substituted C$_{1-4}$ hydroxyalkyl, C$_{1-4}$ alkylcarboxylic acid or substituted C$_{1-4}$ alkylcarboxylic acid;

each R$_{20}$ is independently H, halo, CH$_3$, OCH$_3$, or NO$_2$;

each R$_{21}$ is independently H or CH$_3$;

n is 1 or 2; and

X is a selected from —O—,

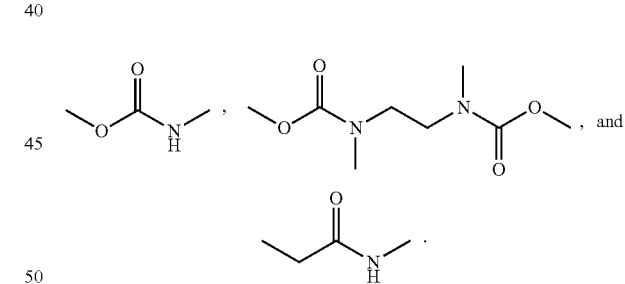

These compounds include, but are not limited to, the following compounds:

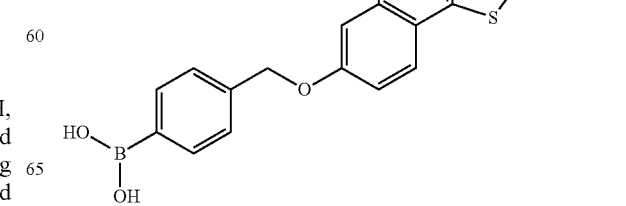

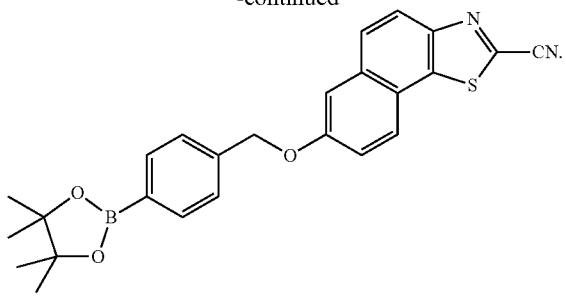

Isomers, Salts and Protected Forms

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half-chair forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and parramethoxyphenyl).

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallization and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below. It may be convenient or desirable to prepare, purify, and/or handle a corresponding salt of the active compound, for example, a pharmaceutically-acceptable salt. Examples of pharmaceutically acceptable salts are discussed in Berge et al., J. Pharm. Sci., 66:1-19 (1977).

For example, if the compound is anionic, or has a functional group which may be anionic (e.g., —COOH may be —COO—), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)$CH_3$, —OAc). For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. For example, an amine group may be protected, for example, as an amide or a urethane, for example, as: a methyl amide (—NHCO—CH₃); a benzyloxy amide (—NHCO—OCH₂C₆H₅, —NHCbz); as a t-butoxy amide (—NHCO—OC(CH₃)₃, —NH-Boc); a 2-biphenyl-2-propoxy amide (—NHCO—OC(CH₃)₂C₆H₄C₆H₅, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide.

For example, a carboxylic acid group may be protected as an ester for example, as: an $C_{1-7}$ alkyl ester (e.g., a methyl ester; a t-butyl ester); a $C_{1-7}$ haloalkyl ester (e.g., a $C_{1-7}$ trihaloalkylester); a tri$C_{1-7}$ alkylsilyl-$C_{1-7}$ alkyl ester; or a $C_{5-20}$ aryl-$C_{1-7}$ alkyl ester (e.g., a benzyl ester; a nitrobenzyl ester); or as an amide, example e.g., as a methyl amide.

For example, a thiol group may be protected as a thioether (—SR), for example, as: a benzyl thioether; or an acetamidomethyl ether (—S—CH₂NHC(=O)CH₃).

Synthesis

Uses of the Compounds

The compounds of the invention may be used in any way that luciferase substrates, e.g., luciferins, have been used. For example, they may be used in a bioluminogenic method which employs an analog of luciferin to detect one or more molecules in a sample, e.g., an enzyme, a cofactor for an enzymatic reaction, an enzyme substrate, an enzyme inhibitor, an enzyme activator, or OH radicals, or one or more conditions, e.g., redox conditions. The sample may include an animal (e.g., a vertebrate), a plant, a fungus, physiological fluid (e.g., blood, plasma, urine, mucous secretions and the like), a cell, a cell lysate, a cell supernatant, or a purified fraction of a cell (e.g., a subcellular fraction). The presence, amount, spectral distribution, emission kinetics, or specific activity of such a molecule may be detected or quantified. The molecule may be detected or quantified in solution, including multiphasic solutions (e.g., emulsions or suspensions), or on solid supports (e.g., particles, capillaries, or assay vessels). In some embodiments the luciferin derivative Scheme 1

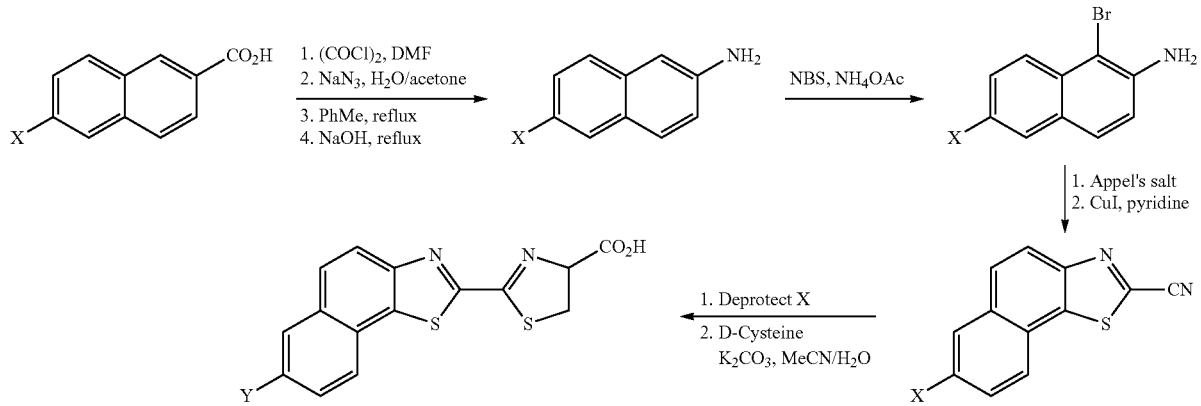

A general synthetic route is shown in Scheme 1. The appropriately substituted 2-naphthoic acid can be converted to a 2-naphthylamine by conversion to the acyl azide and subsequent Curtius rearrangement to the 2-naphthylamine. Electrophilic aromatic halogenation installs a halogen substituent preferentially at the 1-position. Treatment with Appel's salt followed by copper iodide-mediated cyclization affords the 2,1-naphthothiazole core structure which can then be elaborated to the luciferin substrate by reaction with D-cysteine under mild aqueous conditions.

As can be appreciated by the skilled artisan, alternative methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

can be used in luminescence-based assays to detect an enzyme of interest, e.g., CYP450 enzyme, MAO A or B enzyme, a caspase, etc.

In some embodiments, a derivative of luciferin can be used as a probe of a specific biochemical activity, e.g., apoptosis and drug metabolism. In some embodiments, the luciferin concentration is coupled to a specific enzyme activity by a "pro-luciferin" or "pro-substrate" that can be acted on by the specific enzyme of interest. In some embodiments, the pro-luciferin is a molecule that cannot support luminescence directly when combined with luciferase, but can be converted into luciferin through catalytic processing by a specific enzyme of interest. In some embodiments, the approach can be used for enzymes such as those used in drug metabolism, e.g., cytochrome P450 enzymes, monoamine oxidase, and glutathione S-transferase; and apoptosis, e.g., caspases. For example, the luciferin derivatives of the present invention can be modified to contain a cleavable group, such as 6'-O-methyl. In some embodiments, when incubated with a specific cytochrome P450 enzyme, the 6'O-methyl is cleaved, and the pro-luciferin is converted to luciferin which can be detected with a luciferase. In some embodiments, the pro-luciferin can be combined with other components necessary to support luminescence to provide a single reagent and a homogeneous assay. For example, when the reagent is added to a sample, luminescence is generated as pro-luciferin is converted to luciferin. In various embodiments, similar assays can be developed for other enzymes, small molecules, or other cellular processes that can be linked to the generation of luciferins from pro-luciferins.

The luciferin derivatives of the present invention may be used in assay reagents to detect the presence or activity of non-luminescent enzymes such as cytochrome P450 enzymes, proteases or glycosidases. Assays using luminescent enzymes and their substrates are well known in the art. For example, a luminescent enzyme, a luminescent reaction mixture and a luciferin derivative that is a substrate of the non-luminescent enzyme may be added to a sample suspected of containing the non-luminescent enzyme. If the non-luminescent enzyme is present in the sample, the non-luminescent enzyme will act on the luciferin derivative to derive a substrate recognized by the luminescent enzyme to produce a luminescent signal. Alternatively, the non-luminescent enzyme may convert a luminogenic luciferin derivative to a non-luminescent form, i.e., in a loss of signal assay.

The luciferin derivative may be added to the sample prior to or at the same time as the luminescent enzyme. In certain embodiments, the sample may be a cell. Cells may be eukaryotic cells, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may have been genetically modified via recombinant techniques. In certain aspects, the cell may be in an animal, e.g., transgenic animals, or physiological fluid, e.g., blood, plasma, urine, mucous secretions or the like.

The sample may contain more than one non-luminescent enzyme to be detected. In some embodiments, more than one luminescent enzyme may be used. In addition, more than one substrate may be used. Multiple substrates and/or luminescent enzymes may be used to detect multiple non-luminescent enzymes or other molecule(s) of interest, e.g. test compounds, at the same time, e.g. in a multiplex reaction.

The luciferin derivatives are also useful in in situ methods of analyzing cells. Methods of performing in situ analysis of cells using a luciferase are known in the art, see e.g. U.S. Pat. No. 5,998,204. The luciferin derivatives are not substrates of the luminescent enzymes prior to exposure to a non-luminescent enzyme. However, upon exposure to the non-luminescent enzyme, the derivatives are converted into compounds that can be readily detected in a light-emitting reaction in the presence of a luminescent enzyme. Thus, it may be determined where the non-luminescent enzyme is located in a cell by in situ imaging. This may be done by contacting a cell expressing a luminescent enzyme with a luciferin derivative.

Alternatively, a transgenic animal expressing a gene for a luminescent enzyme can be administered a luciferin derivative that is a substrate for a particular non-luminescent enzyme of interest. Imaging technology (e.g. in vivo biophotonic imaging) can then be used to measure luminescence at the site of luminescent enzyme expression in the living, intact animal. Thus, a transgenic animal expressing a luminescent enzyme may be administered a luciferin derivative that will be converted into a substrate for the luminescent enzyme in tissues where the appropriate non-luminescent enzyme of interest is expressed. If the luminescent enzyme is also expressed in that tissue, a luminescent signal will be produced and can be detected by any suitable means. Thus, test compounds, e.g. drugs, can be tested in an animal-based assay. The test compound should be administered to the animal prior to the luciferin derivative. Alternatively, tissue from transgenic animals can be used in tissue based assay.

In some embodiments, a non-transgenic animal may be administered a luciferin derivative that is a substrate for a particular non-luminescent enzyme of interest. The derivative will be converted into a substrate for a luminescent enzyme in tissues where the appropriate non-luminescent enzyme is expressed. A biological sample, e.g., blood, serum, bile, urine, feces, or tissue, can be obtained from the animal and contacted with a luminescent enzyme. The resulting signal can be detectable by any suitable means. Thus, test compounds, e.g. drugs, can be tested in an animal-based assay. The test compound should be administered to the animal prior to the luciferin derivative.

In some embodiments, test compounds such as candidate drugs can be screened and evaluated for their activities as, e.g., (1) substrates of a non-luciferase enzyme, (2) regulators, e.g. inhibitors, inducers or activators, of a non-luciferase enzyme, or (3) modifiers of a cellular condition (e.g., viability, increasing reactive oxygen species, or increasing reducing potential). The luciferin derivatives may also be used to distinguish between substrates and inhibitors of a non-luciferase enzyme. The screening may be performed either in vitro or in vivo.

In addition, for any of the bioluminogenic assays described herein, other reagents may be added to reaction mixtures, including but not limited to those that inhibit or prevent inactivation of luciferase, or otherwise extend or enhance luminescent signal.

Kits

The invention also provides kits. The kit may include one or more of the following: luciferin derivative(s) of which one or more are of the present invention, non-luciferase enzyme(s), luciferin-dependent luminescent enzyme(s), and reaction buffer(s). The reaction buffers may be present in individual formulations for the non-luciferase enzyme reactions and the luminescent enzyme reactions or in a single formulation for a single step assay. The kits of the present invention may also contain inhibitors, activators and/or enhancers for a non-luciferase enzyme(s). The kits of the present invention may also contain a positive and/or negative control for the assay.

The invention is further described by the following non-limiting examples.

EXAMPLES

All chemicals were purchased from Sigma Aldrich or TCI America and used without further purification. Appel's salt and 6-((tert-butoxycarbonyl)amino)-2-naphthoic acid were synthesized as reported elsewhere. (See, Cuadro, A. M.; Alvarez-Builla, J. 4,5-Dichloro-1,2,3-dithiazolium Chloride (Appel's Salt): Reactions with N-nucleophiles, *Tetrahedron* 1994, 50(33), 10037-10046 and Cho, S. J.; Ahn, Y.-H.; Maiti, K. K.; Dinish, U. S.; Fu, C. Y.; Thoniyot, P.; Olivo, M.; Chang, Y.-T. Chem Comm 2010, 46, 722-724, both of which are incorporated by reference herein). Preparation of 6-methoxy-2-naphthylamine has been reported, but can also be accomplished in a manner analogous to 6-((tert-Butoxycarbonyl)amino)-2-naphthylamine Silica gel chromatography was performed on a Teledyne Isco Combiflash system. NMR spectra were acquired on a Varian Mercury 300 MHz system and referenced to internal solvent peaks. Reactions were analyzed on an Agilent 1100 Series analytical HPLC operated with EZChrome software, and preparative HPLC was performed on a Waters HPLC system with dual-wave-

Example 1

Synthesis of 2-(7-Hydroxynaphtho[2,1-d]thiazol-2-yl)-4,5-dihydrothiazole-4-carboxylic acid

1-Bromo-6-methoxy-2-naphthylamine

6-Methoxy-2-naphthylamine (400 mg, 1.6 mmol) was suspended in 20 mL of MeCN with 12 mg of NH$_4$OAc (0.16 mmol) and stirred in an ice bath. N-Bromosuccinimide (299 mg, 1.68 mmol) was dissolved in 6 mL of dry MeCN and added slowly over 1 hour (h). The reaction was stirred for an additional hour at 0° C., then adsorbed onto Celite, concentrated under reduced pressure and subjected to silica gel chromatography eluting with 0→60% EtOAc in heptanes to yield 300 mg of an orange solid. 7.94 (d, 1H); 7.55 (d, 1H); 7.18 (dd, 1H); 7.09 (d, 1H); 7.02 (d, 1H); 4.29 (br s, 2H); 3.89 (s, 3H).

7-Methoxynaphtho[2,1-d]thiazole-2-carbonitrile

1-Bromo-6-methoxy-2-naphthylamine (290 mg, 1.15 mmol) was stirred in 10 mL of dry DCM, and Appel's salt (252 mg, 1.21 mmol) was added. After stirring for 24 h at room temperature (RT), the reaction was diluted with EtOAc and washed with water, dried over Na$_2$SO$_4$ and adsorbed onto Celite. Silica gel chromatography eluting with 0→40% EtOAc in heptanes afforded 228 mg of the desired adduct, which was taken up in 5 mL of pyridine and treated with 168 mg (0.882 mmol) of CuI. The reaction was heated to reflux for 1.5 h, then adsorbed onto Celite and 63 mg of the desired product was obtained by silica gel chromatography eluting with 0→40% EtOAc in heptanes. $^1$H NMR (CD$_2$Cl$_2$) d 8.12 (d, 1H); 8.01 (d, 1H); 7.94 (d, 1H); 7.39 (d, 1H); 7.35 (dd, 1H); 3.99 (s, 3H).

7-Hydroxynaphtho[2,1-d]thiazole-2-carbonitrile

7-Methoxynaphtho[2,1-d]thiazole-2-carbonitrile (88 mg, 0.366 mmol) was suspended in 3 g of pyridine hydrochloride salt and sealed in a 5-mL microwave vial containing a stir bar. The mixture was irradiated at 220° C. for 25 minutes (min), then taken up in 1 N HCl and extracted three times with a mixture of DCM and EtOAc. The concentrated residue was purified by silica gel chromatography. $^1$H NMR (CD$_2$Cl$_2$) d 8.10 (d, 1H); 8.03 (d, 1H); 7.88 (d, 1H); 7.39 (d, 1H); 7.31 (dd, 1H);

2-(7-Hydroxynaphtho[2,1-d]thiazol-2-yl)-4,5-dihydrothiazole-4-carboxylic acid A solution of 7-hethoxynaphtho[2,1-d]thiazole-2-carbonitrile (35 mg, 0.155 mmol) in acetonitrile was treated with an aqueous solution containing D-cysteine (54 mg, 0.309 mmol) and K$_2$CO$_3$ (54 mg, 0.391 mmol). After stirring at RT for 20 min, the reaction was neutralized by addition of AcOH, and the product was isolated by preparative HPLC eluting with a gradient of 5→95% MeCN in 10 mM aqueous NH$_4$OAc. The appropriate fractions were concentrated under reduced pressure and then lyophilized. $^1$H NMR (DMSO-d$_6$/MeCN-d$_3$) d 8.53 (d, 1H); 8.48 (d, 1H); 8.31 (d, 1H); 7.82-7.86 (m, 2H); 5.77 (dd, 1H); 4.33 (dd, 1H); 4.19 (dd, 1H).

Example 2

2-(7-aminonaphtho[2,1-d]thiazol-2-yl)-4,5-dihydrothiazole-4-carboxylic acid tert-Butyl (6-(azidocarbonyl)naphthalen-2-yl)carbamate 2-(t-Butylcarbamoyl)amino-6-naphthoic acid (1.35 g, 4.7 mmol) was stirred in 20 mL of DCM in an ice bath. DMF (0.2 mL) was added, and then oxalyl chloride (420 uL, 630 mg, 4.9 mmol) added slowly. After 45 min, the reaction was concentrated under reduced pressure, and the residue was taken up in acetone. Sodium azide (916 mg, 14.1 mmol) was added as a solution in H$_2$O, and the reaction was stirred for 15 min. The desired product was precipitated by the addition of more H$_2$O and isolated by filtration to yield 1.26 of a slightly pink solid. $^1$H NMR (DMSO-d$_6$) 9.81 (s, 1H); 8.51 (s, 1H); 8.19 (d, 1H); 8.04 (d, 1H); 7.84-7.91 (m, 2H); 7.59 (dd, 1H); 1.50 (s, 9H).

tert-Butyl (6-aminonaphthalen-2-yl)carbamate tert-Butyl (6-(azidocarbonyl)naphthalen-2-yl)carbamate (2.7 g, 8.64 mmol) in 75 mL of toluene was heated to reflux for 2 h. A 6 M solution (10 mL, 60 mmol) of aqueous NaOH was added, and the reaction was heated at reflux for 72 h. The reaction was cooled to RT and filtered. The filtrate was extracted with 3×EtOAc, and the combined organic layers dried over Na$_2$SO$_4$ and evaporated to yield 1.62 g of a slightly pink solid. The product could be purified further by silica gel chromatography eluting with a gradient of 0→60% EtOAc in heptanes. $^1$H NMR (CD$_2$Cl$_2$) d 7.80 (br s, 1H); 7.58 (d, 1H); 7.52 (d, 1H); 7.27 (dd, 1H); 6.92-6.98 (m, 2H); 6.59 (br s, 2H); 1.53 (s, 9H).

tert-Butyl (6-amino-5-bromonaphthalen-2-yl)carbamate tert-Butyl (6-aminonaphthalen-2-yl)carbamate (1.31 g, 5.07 mmol) was stirred with ammonium acetate (39 mg, 0.5 mmol) in MeCN in an ice bath. N-Bromosuccinimide (948 mg, 5.32 mmol) was dissolved in additional MeCN and added slowly over 1 h. Stirring was continued for 1 h at 0° C., and then Celite was added. Solvents were removed under reduced pressure, and the product (1.33 g, 78%) isolated by silica gel chromatography eluting with a gradient of 0→50% EtOAc in heptanes. $^1$H NMR (CD$_2$Cl$_2$) d 7.94 (d, 1H); 7.89 (br d, 1H); 7.58 (d, 1H); 7.38 (dd, 1H); 7.02 (d, 1H); 6.66 (br s, 1H); 4.35 (br s, 2H); 1.54 (s, 9H).

tert-Butyl (2-cyanonaphtho[2,1-d]thiazol-7-yl)carbamate

To a stirred solution of tert-butyl (6-amino-5-bromonaphthalen-2-yl)carbamate (540 mg, 1.6 mmol) in dry DCM, 351 mg of Appel's salt (1.68 mmol) was added. Upon completion, the reaction was diluted with EtOAc and washed with water. The organic layer was dried over Na$_2$SO$_4$ and evaporated. The crude material thus obtained was dissolved in 10 mL of pyridine and treated with 529 mg (2.78 mmol) of CuI. The reaction was heated in a 110° C. oil bath for 40 min, and then the solvents were removed under reduced pressure. The resulting solids were taken up in EtOAc and filtered. The filtrate was washed with 1 N HCl, the aqueous layer extracted with 2×EtOAc, and the combined organic layers dried over Na$_2$SO$_4$. The solvents were removed under reduced pressure, and the resulting material subjected to silica gel chromatography eluting with 15→35% EtOAc in heptanes to yield 148 mg of a yellow solid. $^1$H NMR (CD$_2$Cl$_2$) d 8.21 (d, 1H); 8.12 (d, 1H); 8.03 (d, 1H); 7.96 (d, 1H); 7.64 (dd, 1H); 6.90 (br s, 1H); 1.55 (s, 9H).

7-aminonaphtho[2,1-d]thiazole-2-carbonitrile

To a stirred solution of tert-butyl (2-cyanonaphtho[2,1-d]thiazol-7-yl)carbamate (72 mg, 0.22 mmol) and thioanisole (0.5 mL) in 2 mL of DCM in an ice bath, 2 mL of trifluoroacetic acid was added. After 1 h, the reaction was concentrated under reduced pressure, and the product (47 mg, 94%) was isolated by silica gel chromatography eluting with 0→75% EtOAc in heptanes. $^1$H NMR (CD$_2$Cl$_2$) d 8.01 (d, 1H); 7.90 (dt, 1H); 7.76 (d, 1H); 7.09-7.16 (m, 2H).

2-(7-aminonaphtho[2,1-d]thiazol-2-yl)-4,5-dihydrothiazole-4-carboxylic acid

A solution of 7-aminonaphtho[2,1-d]thiazole-2-carbonitrile (24 mg, 0.106 mmol) in acetonitrile was treated with an aqueous solution containing D-cysteine (41 mg, 0.233 mmol) and K$_2$CO$_3$ (45 mg, 0.326 mmol). After stirring at RT for 20 min, the product was isolated by preparative HPLC eluting with a gradient of 5→100% MeCN in 10 mM aqueous NH$_4$OAc. The appropriate fractions were concentrated under reduced pressure and then lyophilized to afford 12 mg of a yellow solid. $^1$H NMR (DMSO-d$_6$) d 7.77-7.87 (m, 2H); 7.59 (d, 1H); 7.01 (dd, 1H); 6.94 (d, 1H); 5.69 (br s, 2H); 5.18 (t, 1H); 3.57-3.68 (m, 2H).

Example 3

Synthesis of 2-(7-Hydroxynaphtho[2,1-d]thiazol-2-yl)-4,5-dihydrothiazole-4-carboxylic acid methyl ester 2-(7-Hydroxynaphtho[2,1-d]thiazol-2-yl)-4,5-dihydrothiazole-4-carboxylic acid methyl ester 2-(7-Hydroxynaphtho[2,1-d]thiazol-2-yl)-4,5-dihydrothiazole-4-carboxylic acid (8 mg, 24 umol) was suspended in a mixture of MeCN and MeOH and acidified to pH<3 by the addition of TFA. The solution was treated with a solution of diazomethane in ether until the yellow color persisted. Excess diazomethane was neutralized by the addition of AcOH, the ether removed under reduced pressure, and the desired product (3.3 mg) isolated as a yellow solid by preparative HPLC eluting with 5→100% MeCN in NH4OAc, followed by lyophilization. Calcd for C$_{16}$H$_{13}$N$_2$O$_3$S$_2$ (M+H): 345.0. found 345.

Example 4

Synthesis of 2-(7-(Leucinyl)aminonaphtho[2,1-d]thiazol-2-yl)-4,5-dihydrothiazole-4-carboxylic acid 7-(Boc-leucinyl)aminonaphtho[2,1-d]thiazole-2-carbonitrile Boc-protected leucine (108 mg, 0.47 mmol) was dissolved in 5 mL of THF in a dry ice-ethylene glycol bath and treated first with N-methyl morpholine (100 uL, 0.93 mmol), then with isobutyl chloroformate (50 uL, 0.51 mmol). The reaction was stirred for 15 min, and a solution of 7-aminonaphtho[2,1-d]thiazole-2-carbonitrile (70 mg, 0.31 mmol) in 5 mL of THF added. The reaction was transferred to an ice bath and allowed to stir for 72 h with concomitant warming to RT. The reaction was diluted with DCM and washed with 1 N HCl, the aqueous layer was extracted with 2×DCM, and the combined organic layers dried over Na$_2$SO$_4$ and adsorbed onto Celite. Silica gel purification eluting with 0→60% EtOAc in heptanes afforded 117 mg of the desired product. $^1$H NMR (CD$_2$Cl$_2$) d 8.75 (br s, 1H); 8.40 (s, 1H); 8.09 (d, 1H); 8.01 (d, 1H); 7.93 (d, 1H); 7.70 (d, 1H); 5.00 (br s, 1H); 4.29 (br s, 1H); 1.72-1.87 (m, 2H); 1.56-1.66 (m, 1H); 1.48 (s, 9H); 1.01 (pseudo tr, 6H).

2-(7-(Leucinyl)aminonaphtho[2,1-d]thiazol-2-yl)-4,5-dihydrothiazole-4-carboxylic acid 7-(Boc-leucinyl)aminonaphtho[2,1-d]thiazole-2-carbonitrile (69 mg, 0.16 mmol) was combined with 0.5 mL of thioanisole and 1.5 mL of DCM and stirred in an ice bath. Trifluoroacetic acid (1.5 mL) was added, and the reaction monitored by HPLC. After 1 h, solvents were removed under reduced pressure, and the remaining residue triturated with ether. The resulting solid was taken up in MeCN/H$_2$O and treated with D-cysteine hydrochloride hydrate (55 mg, 0.31 mmol) and potassium carbonate (55 mg, 0.40 mmol). After 20 min, the reaction was filtered and the product was isolated by preparative HPLC eluting with 2→50% MeCN in 0.1% formic acid. Calcd for C$_{21}$H$_{23}$N$_4$O$_3$S$_2$ (M+H): 443.1. found 443.

Example 5

Titation of Amino-Peptidase with PBI-5044

To a lyophilized vial of luciferin detection reagent (Promega; V859A), 10 ml of a solution of 100 mM HEPES pH 7.5/10 mM MgSO4 was added and allowed to equilibrate for 30 minutes at room temperature.

A 20 uM solution of Leu-luciferin and a 20 uM solution of PBI-5044 were prepared in a solution of 100 mM HEPES/0.1% Prionex. The 20 uM solution of PBI-5044 was then serially diluted in the HEPES/Prionex solution to 2 uM and 0.2 uM solutions.

1 U/ml Leu-aminopeptidase (Sigma) was serially diluted (FIG. 1) into each of the luciferin dilutions (20 uM Leu-luciferin, 20 uM PBI-5044, 2 uM PBI-5044 or 0.2 uM PBI-5044). For example, 50 ul 1 U/ml Leu-aminopeptidase was added to 450 ul luciferin dilution (final concentration of Leu-aminopeptidase was 0.1 U/ml). Leu-aminopeptidase was then serially diluted by adding 150 ul Leu-aminopeptidase solution to 350 ul of each prepared luciferin derivative.

In triplicate, 50 ul of each serially diluted Leu-aminopeptidase/luciferin sample was added to a well of a white, 96-well assay plate (Costar 3355), and 50 ul of the equilibrated luciferin detection reagent added to each sample. Luminescence was detected every 5 minutes for 90 minutes on a GloMax® Multi luminometer (Promega) at room temperature.

Figure 2:
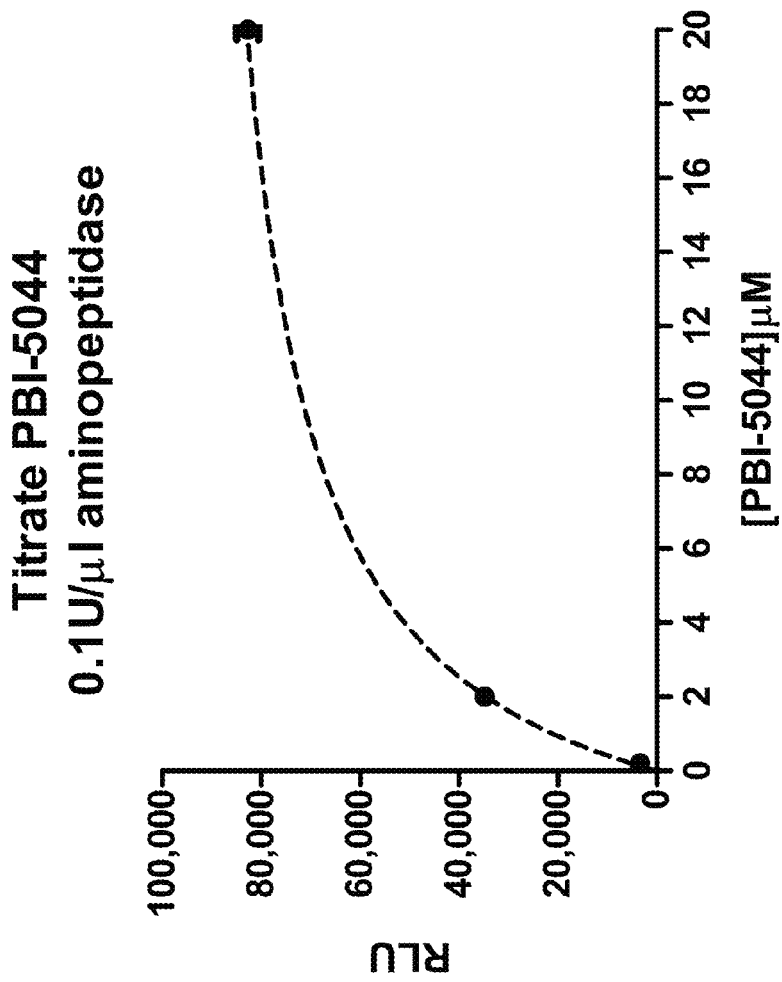
FIG. 2 illustrates the Km of leucinyl aminoisonaphtholuciferin with respect to aminopeptidase.

FIG. 1 shows the bioluminescent response of leucine adducts of aminoluciferin control (Leu-luciferin; black circles) or aminoisonaphtholuciferin (PBI-5044; gray squares) as a function of added aminopeptidase. FIG. 2 shows the Km of leucinyl aminoisonaphtholuciferin with respect to aminopeptidase. These results demonstrate an embodiment of a luminescent peptidyl pro-substrate, and its successful use in reporting protease activity.

Example 6

Multiplexing with Leu-Luciferin and PBI-5044

To a lyophilized vial of luciferin detection reagent (Promega; V859A), 10 ml of a solution of 100 mM HEPES pH 7.5/10 mM MgSO4 was added (LDR) and allowed to equilibrate for 30 minutes at room temperature.

Aminopeptidase was diluted to 0.01 u/ml into a solution containing 100 mM HEPES pH 7.5 and 0.1% Prionex. The following solutions were then prepared in the aminopeptidase dilution:
1. 20 uM Leu-Luciferin,
2. 20 uM PBI-5044,
3. 20 uM Leu-Luciferin/20 uM PBI-5044

In triplicate, 50 ul of each of the above mixtures (1-3) was added to 50 ul of LDR and incubate for 15 minutes. Luminescence was measured on a GloMax® 96 luminometer equipped with a 630 long pass filter (Edmond Optics 253253) and a 525 short pass filter (Edmond Optics 84694).

Figure 3:
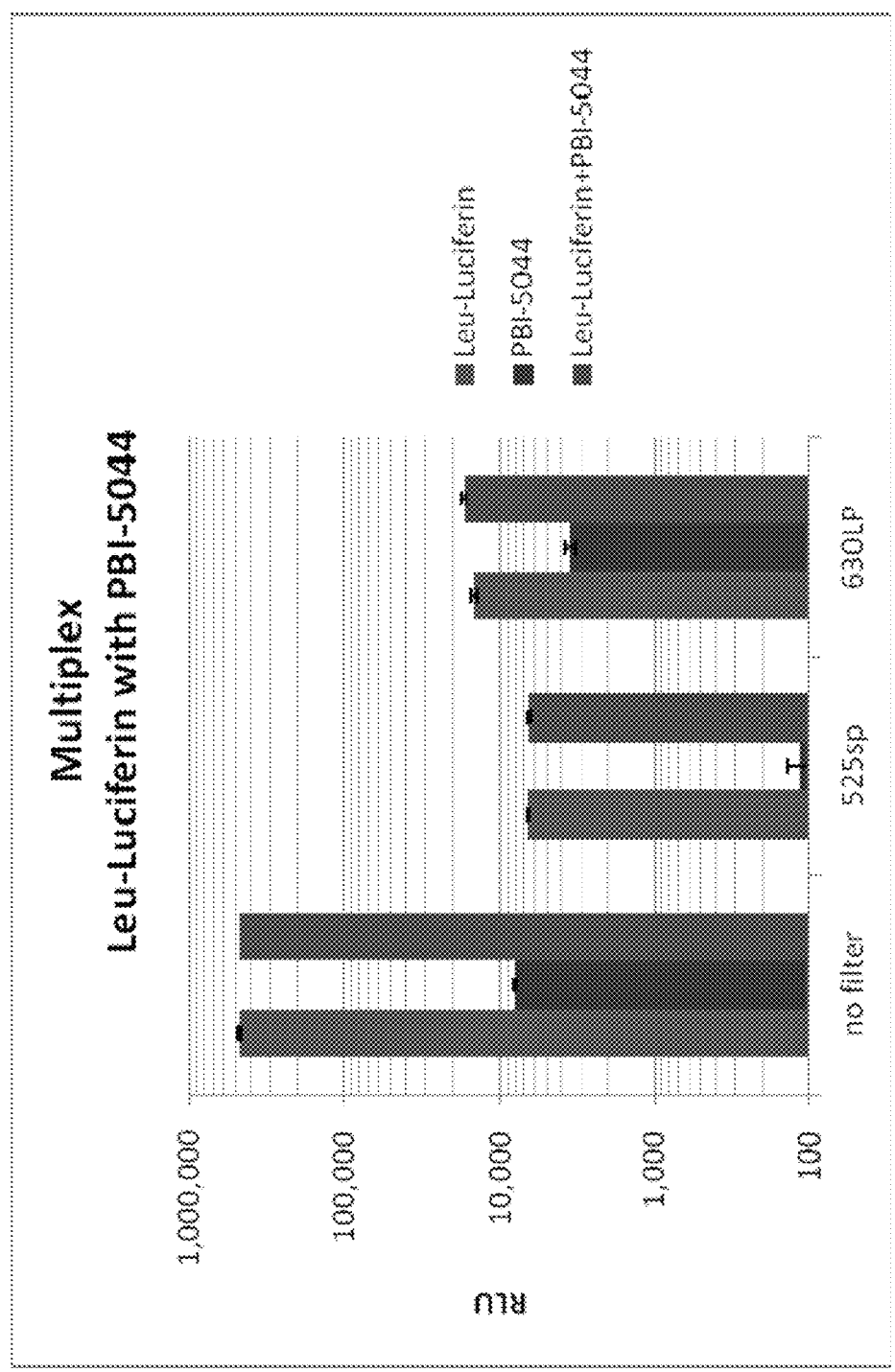
FIG. 3 illustrates that a luciferin substrate (which generates green light) and a substrate of the present invention can be multiplexed, i.e., added to the same sample, and luminescence from each detected with little interference from the other.

FIG. 3 shows the effects of filters on separating bioluminescence of luciferin from aminoisonaphtholuciferin (PBI-5044). These results demonstrate that a luciferin substrate (which generates green light) and a substrate of the present invention can be multiplexed, i.e., added to the same sample, and luminescence from each detected with little interference from the other.

Example 7

Effect of Esterase on the Bioluminescence of PBI-5045

Reconstitution buffer with esterase (10 ml; Promega Cat. No. V144A) and luciferin detection reagent (Promega; V859A) were mixed and incubated at room temperature for 30 minutes ("Luciferin Detection Reagent"). UltraGlo® luciferase (210 ul of 5.7 mg/ml; Promega) was then added to 3 mls of the luciferin detection reagent.

Serial dilutions of PBI-5045 (isonaphtholuciferin methyl ester) were made in a solution of 100 mM HEPES/10 mM MgSO$_4$. 50 ul of each serially diluted PBI-5045 was then added to a well of a white, 96-well assay plate (n=6). Then, either 50 ul luciferin detection reagent or luciferin detection reagent with UltraGlo® luciferase was added to the wells. Luminescence was detected on a GloMax® Multi+ luminometer (Promega).

Figure 4:
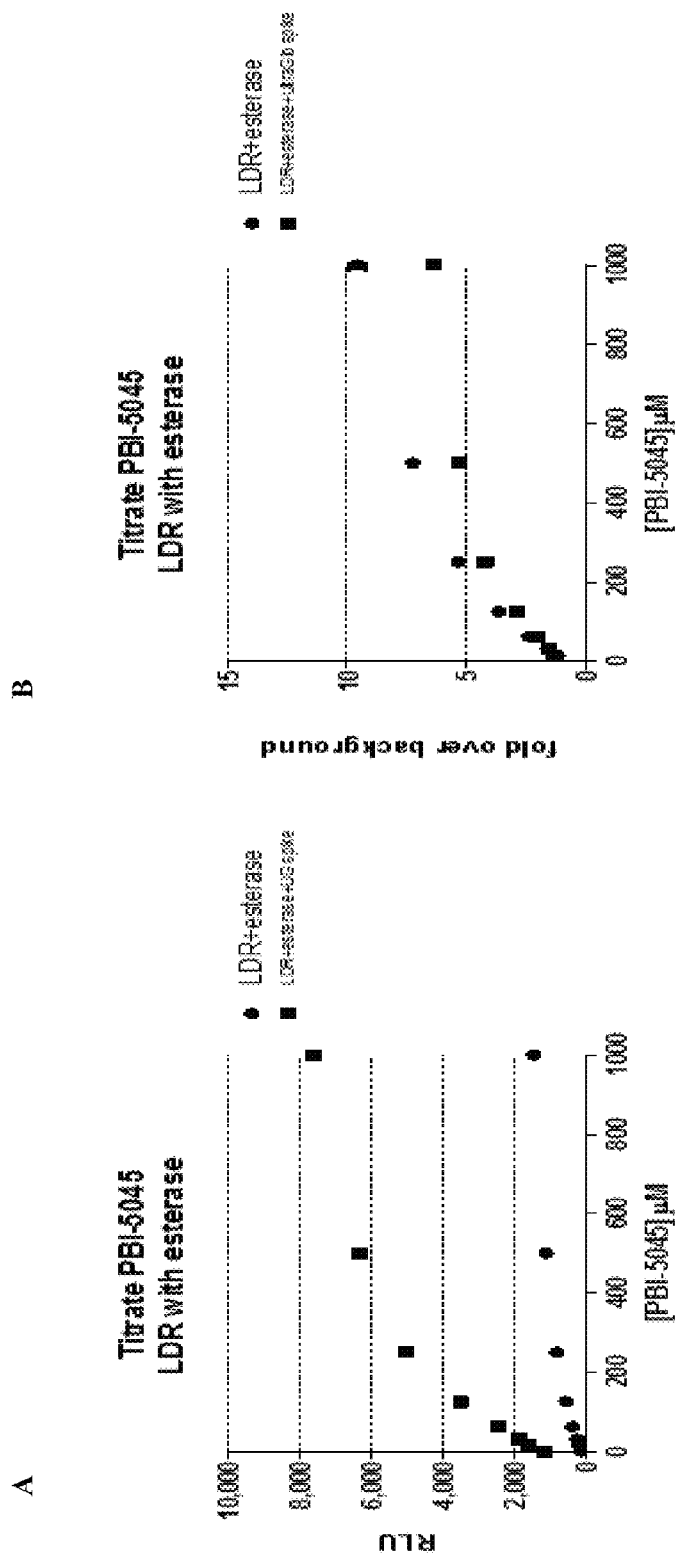
FIG. 4 illustrates use of a luminescent ester pro-substrate, PBI-5045, of the present invention to report esterase activity.

FIGS. 4A and 4B show the effects of esterase on PBI-5045. FIG. 4A shows the luminescence (RLUs), and FIG. 4B shows the fold luminescence over background. These results demonstrate an embodiment of a luminescent ester pro-substrate and its successful use in reporting esterase activity.

Example 8

Cell Toxicity Studies

In this example, the cell toxicity of PBI-4739 or PBI-4813 was examined in HeLa cells.

PBI-4739 or PBI-4813 were prepared at a concentration of 5 mM in DMEM with 10% serum and then two-fold serially diluted in culture medium. The titration series was than added to HeLa monolayers and incubated at 37° C. At 24 hours, the media containing the substrates was replaced with serum free DMEM and toxicity (ATP) was measured by CellTiter-Glo® Luminescent Cell Viability Assay according to the manufacturer's instructions (Promega Corporation).

Figure 5:
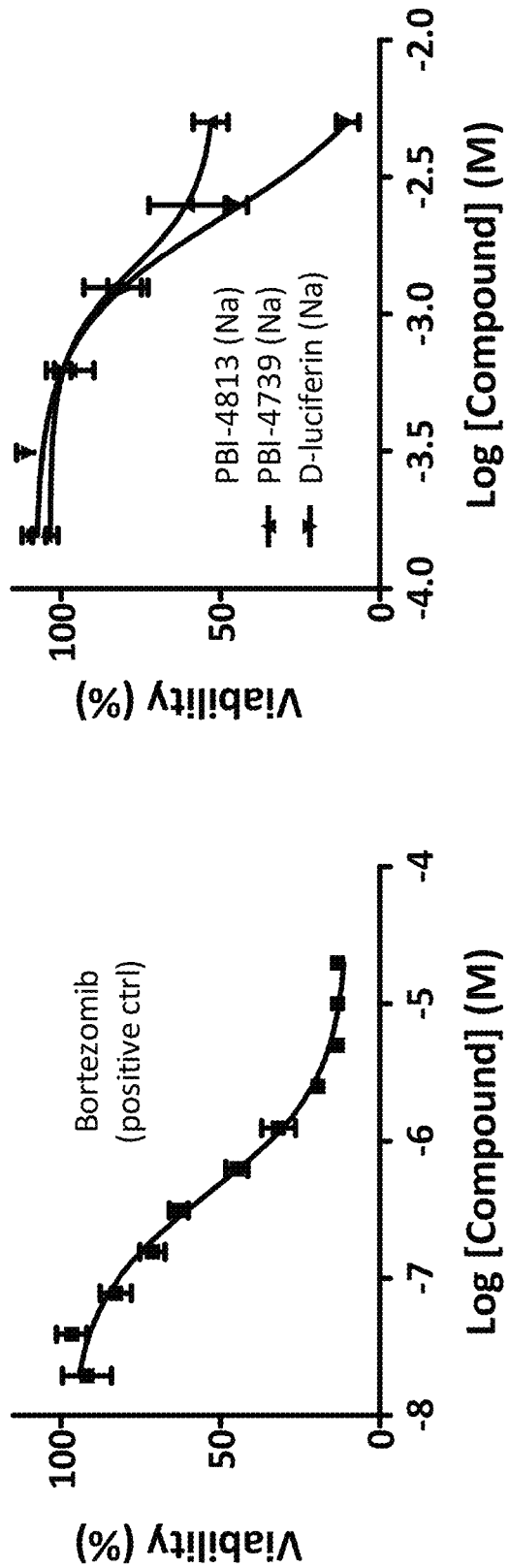
FIG. 5 shows a cytotoxicity profile for PBI-4813 and 4739.
Figure 11:
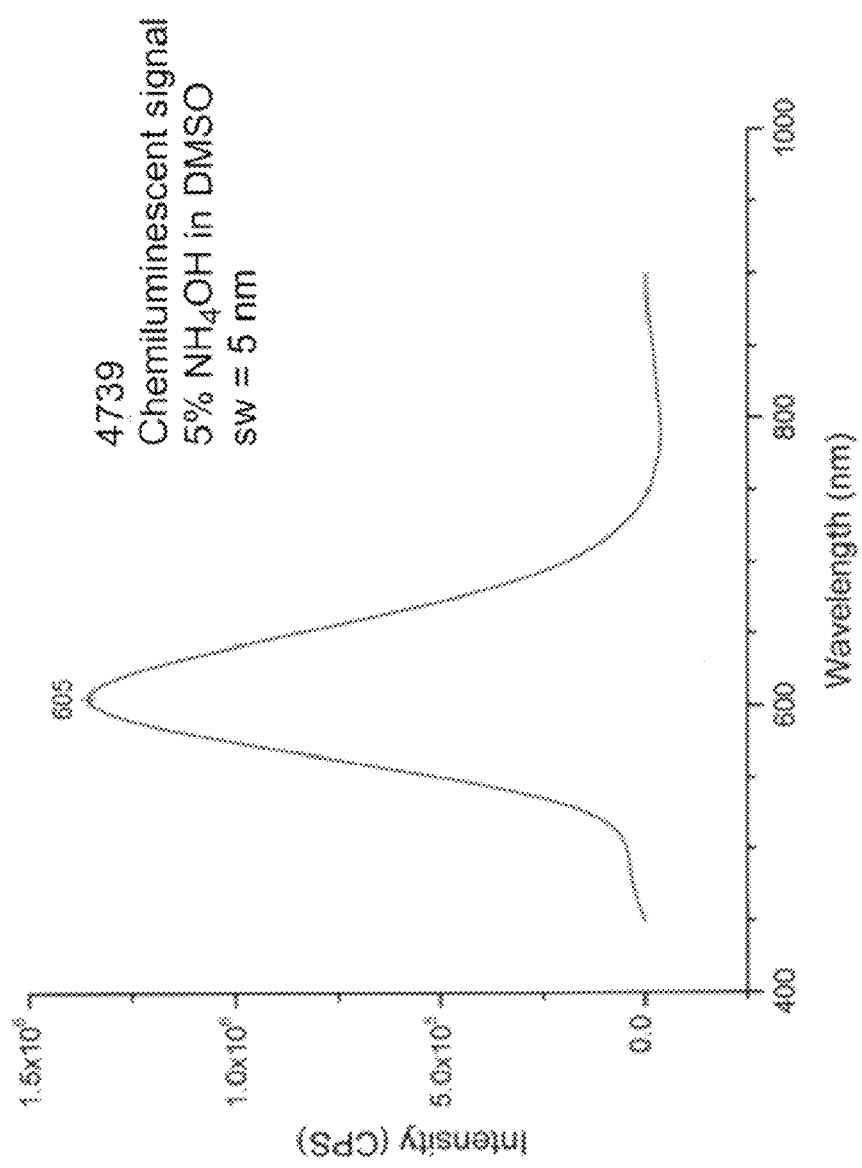
FIG. 11 shows the chemiluminescent signal of PBI-4379.
Figure 12:
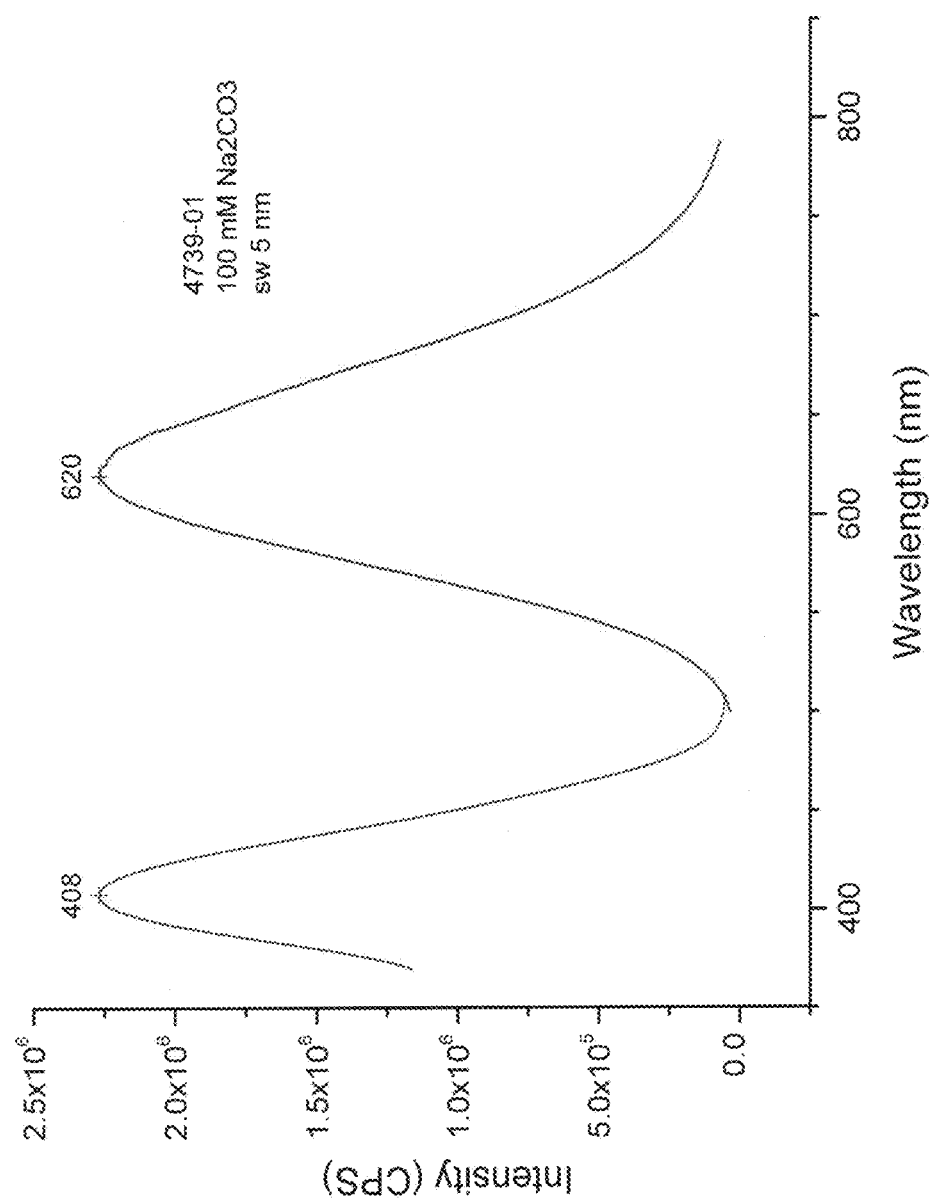
FIG. 12 shows fluorescent data for PBI-4379.
Figure 13:
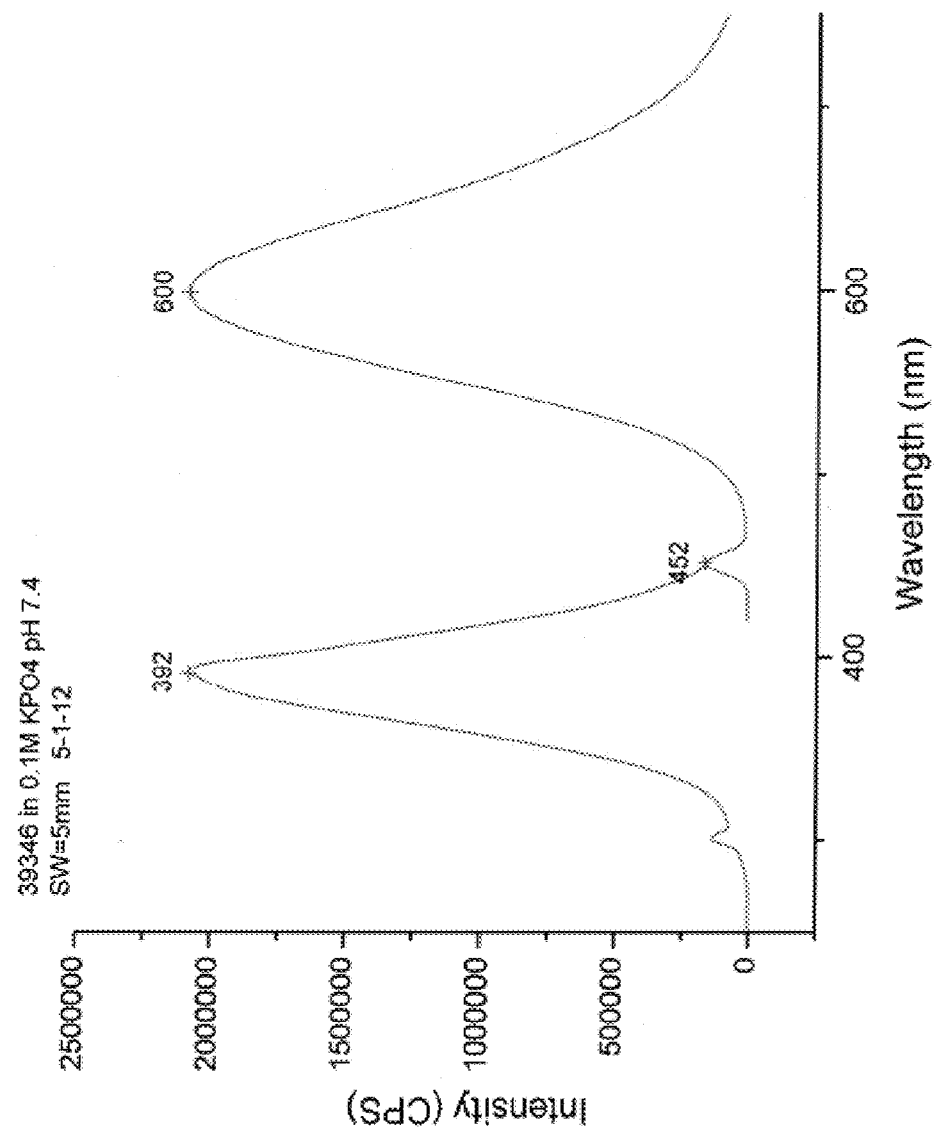
FIG. 13 shows fluorescent data for PBI-4813.

The results show that PBI-4813 and 4739 show a cytotoxicity profile that is comparable to D-luciferin (FIG. 5). D-luciferin is commonly used as a reagent in live animal imaging experiments and is generally considered non-toxic in this setting. This data suggest PBI-4813 and PBI-4739 should also be well-tolerated in animals when used for live animal imaging.

Example 9

Tolerability of a Single Dose of PBI-4739 or PBI-4813 in Female CD-1 Mice

In this example, the tolerability of PBI-4739 or PBI-4813 was examined at different dose levels in female CD-1 mice and compared to D-luciferin.

Three dosages of PBI-4739 or PBI-4813 were administered intraperitoneally as a single dose and compared to 3 dosages of D-luciferin. The animals were monitored for 5 days for clinical findings, behavioral changes and survival. Body weights were monitored daily. Necropsy was performed in the highest does groups for PBI-4739, PBI-4813, D-luciferin and vehicle only (DPBS; Sigma Aldrich). The animals were 40 female, CD-1 mice age 6 weeks with a mean body weight of 27.4+1.6 [SD].

Table 1 lists the dosage groups. Each group contained 4 animals.

TABLE I

Experimental groups

| Group no. | Treatment | Dose | Route | Animals (n) | Animal no. |
|---|---|---|---|---|---|
| 1 | Vehicle | 10 mL/kg | i.p. | 4 | 1-4 |
| 2 | 4739 | 18 mg/kg | i.p. | 4 | 5-8 |
| 3 | 4739 | 35 mg/kg | i.p. | 4 | 9-12 |
| 4 | 4739 | 88 mg/kg | i.p. | 4 | 13-16 |
| 5 | 4813 | 19 mg/kg | i.p. | 4 | 17-20 |
| 6 | 4813 | 71 mg/kg | i.p. | 4 | 21-24 |
| 7 | 4813 | 141 mg/kg | i.p. | 4 | 25-28 |
| 8 | Reference compound | 13 mg/kg | i.p. | 4 | 29-32 |
| 9 | Reference compound | 55 mg/kg | i.p. | 4 | 33-36 |
| 10 | Reference compound | 133 mg/kg | i.p. | 4 | 37-40 |

Under the conditions of the experiment, none of the animals were observed as having any test compound related adverse effects. FIGS. 6-10 provide the data from the clinical signs and animal behavior (FIG. 6), survival rate (FIG. 7), body weights (grams; FIG. 8), body weights (%; FIG. 9) and necropsy results (FIG. 10).

Example 10

Spectral Analysis of PBI-4739 and PBI-4813

For spectral analysis of PBI-4739 and PBI-4813, ATP was added to a concentration of 1 mM to Bright-Glo™ Luciferase Assay Buffer (Promega Corporation Cat. No. E264A). PBI-4739 and PBI-4813 (100 mM DMSO stock) was diluted to 1:100 into Bright-Glo™ Luciferase Assay buffer (1 mM final). 50 ul of each substrate was added to 50 ul of Click Beetle Red purified enzyme (0.5 mg/ml; Promega Corporation) in triplicate and then the samples assayed using a Tecan M-1000 in spectral scan mode using 2 nm steps for 4739 and 5 nm steps for 4813.

Figure 14:
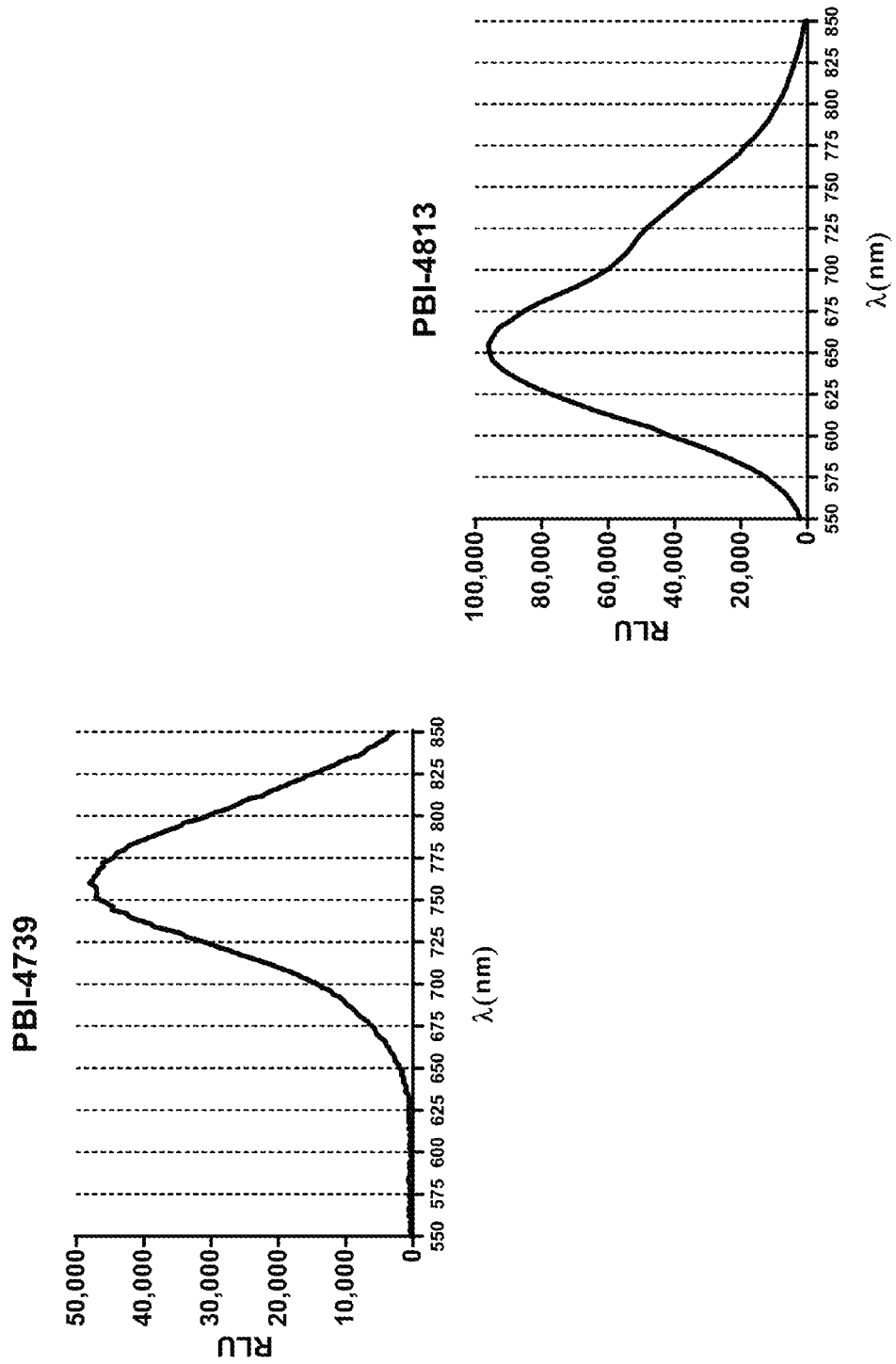
FIG. 14 shows the spectral data for PBI-4739 and PBI-4813 demonstrating their near-IR properties.

FIG. 14 provides the spectral data for the two substrates demonstrating their near-IR properties.

The invention claimed is:

1. A compound according to Formula (Ia):

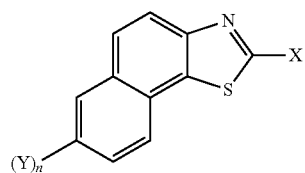
(Ia)

wherein
X is CN or

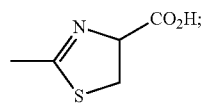

each Y is independently halo, $SO_3H$, $C_{1-4}$ alkyl, substituted $C_{1-4}$ alkyl, $OR^1$ or $NR^1R^2$;
each $R^1$ is H, $C_{1-10}$ alkyl or substituted $C_{1-10}$ alkyl;
each $R^2$ is H, $C_{1-10}$ alkyl or substituted $C_{1-10}$ alkyl; or $R^1$ and $R^2$ together form a 4 to 8 membered ring; and
n is 1 to 6.

2. A compound according to claim 1, wherein at least one Y is OH.

3. A compound according to claim 1, wherein at least one Y is $NR^1R^2$.

4. A compound according to claim 1, wherein at least one Y is OH or $NR^1R^2$ and up to 5 additional Ys are halo groups.

5. A compound according to claim 4, wherein the halo groups are fluoro.

6. A compound according to claim 4, wherein the halo groups are chloro.

7. A compound according to claim 1, wherein at least one Y is $SO_3H$.

8. A compound according to claim 1, wherein the compound is a compound of Formula (II):

(II)

wherein
X is CN or

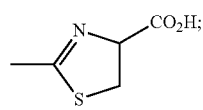

Y is $OR^1$ or $NR^1R^2$;
$R^1$ is H, $C_{1-10}$ alkyl or substituted $C_{1-10}$ alkyl; and
$R^2$ is H, $C_{1-10}$ alkyl or substituted $C_{1-10}$ alkyl; or
$R^1$ and $R^2$ together form a ring.

9. A compound according to claim 1, wherein the compound is a compound of Formula (III):

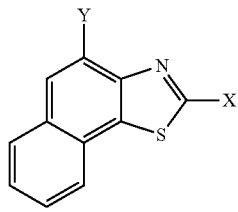
(III)

wherein
X is CN or

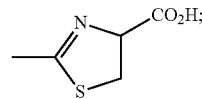

Y is $OR^1$ or $NR^1R^2$;
$R^1$ is H, $C_{1-10}$ alkyl or substituted $C_{1-10}$ alkyl; and
$R^2$ is H, $C_{1-10}$ alkyl or substituted $C_{1-10}$ alkyl; or
$R^1$ and $R^2$ together form a ring.

10. A compound according to claim 1, wherein the compound is a compound of Formula (VII):

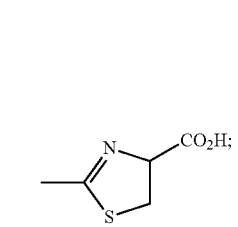
(VII)

wherein
X is CN or

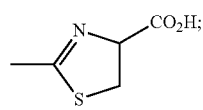

each Y is independently $OR^1$ or $NR^1R^2$;
each $R^1$ is independently H, $C_{1-10}$ alkyl or substituted $C_{1-10}$ alkyl; and
each $R^2$ is independently H, $C_{1-10}$ alkyl or substituted $C_{1-10}$ alkyl; or
$R^1$ and $R^2$ together form a ring.

11. A compound according to claim 1, wherein X is CN.

12. A compound according to claim 1, wherein X is

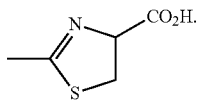

13. A compound according to claim 1, wherein Y is NH₂.

14. A method for detecting luminescence in a sample comprising
   contacting a sample with a compound according to claim 1;
   contacting the sample with a luciferase, if it is not present in the sample; and
   detecting luminescence.

15. The method of claim 14, wherein the sample contains live cells.

16. The method of claim 14, wherein the sample contains a luciferase.

17. A method for detecting luminescence in a transgenic animal comprising
   administering a compound according to claim 1 to a transgenic animal; and
   detecting luminescence;
   wherein the transgenic animal expresses a luciferase.

18. A kit comprising a compound according to claim 1.

19. The kit of claim 18 further comprising a luciferase.

20. The kit of claim 18 further comprising a buffer reagent.

21. A compound selected from the group consisting of:

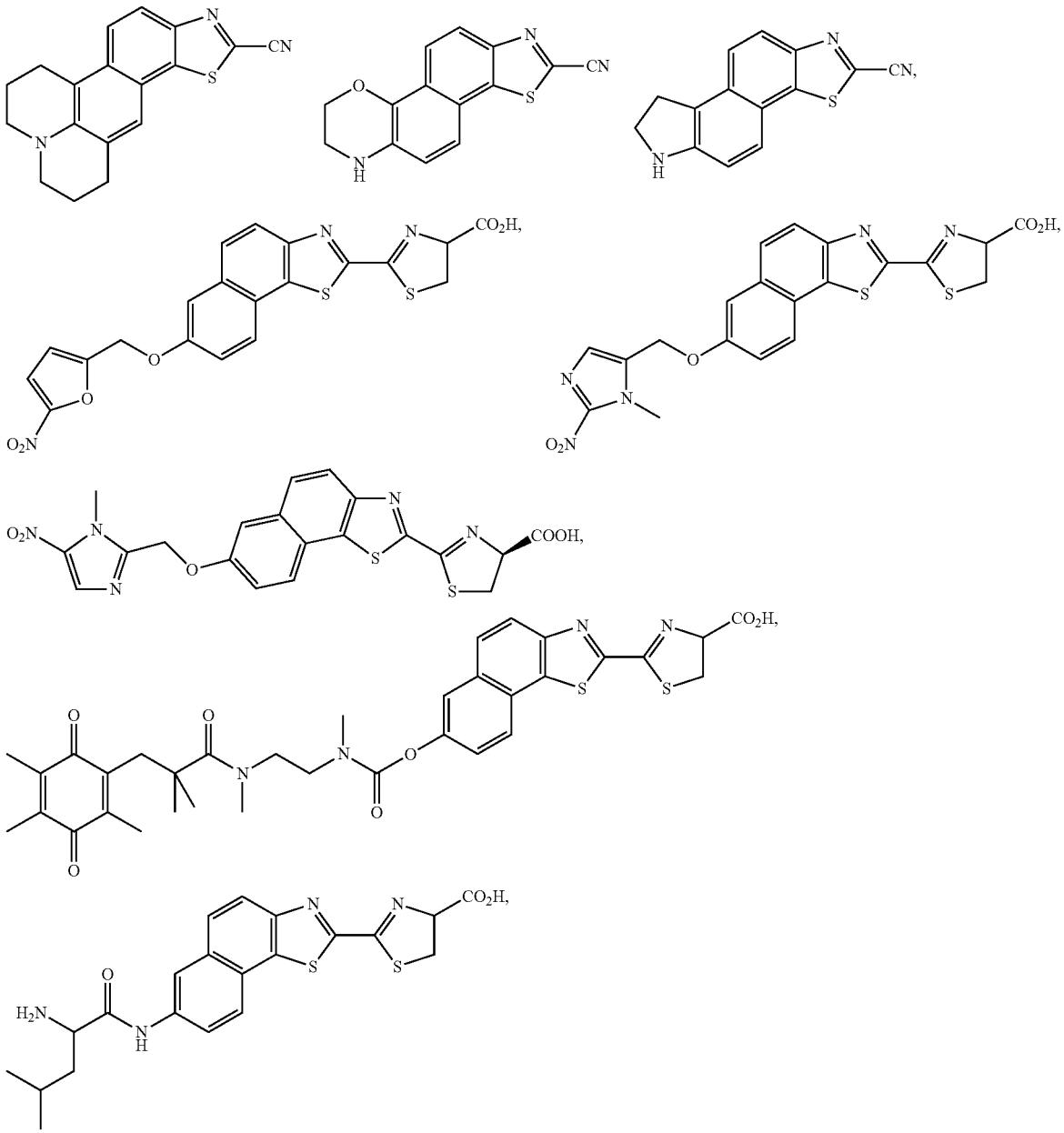

-continued
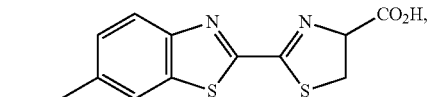
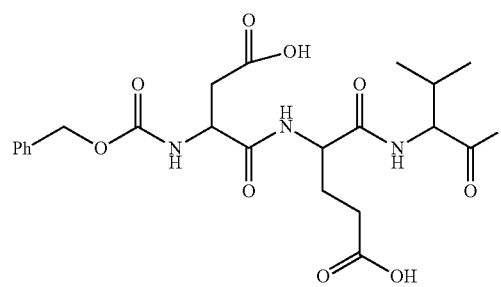
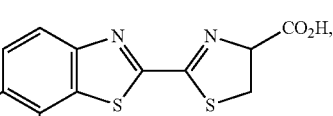
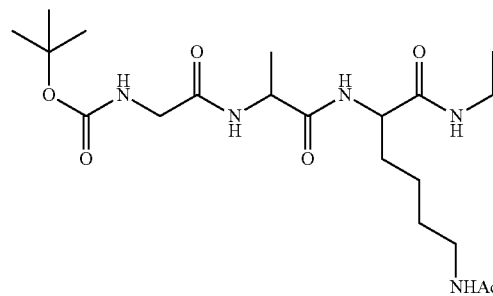
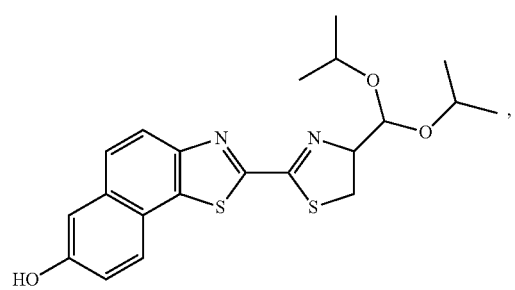
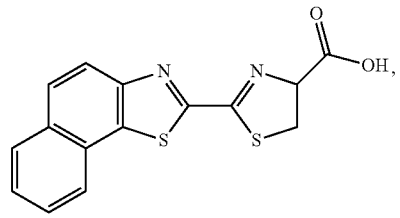
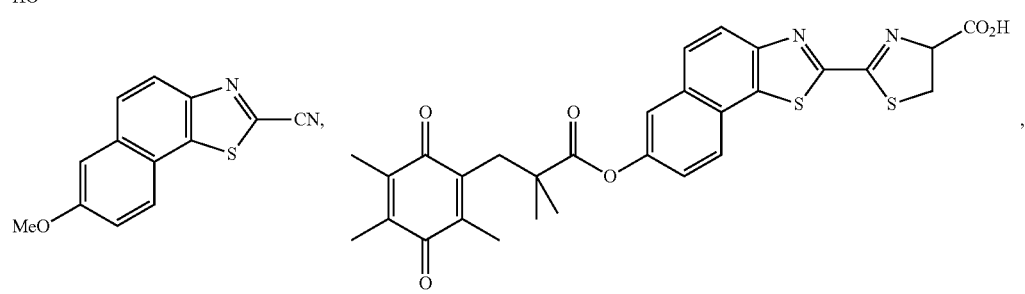
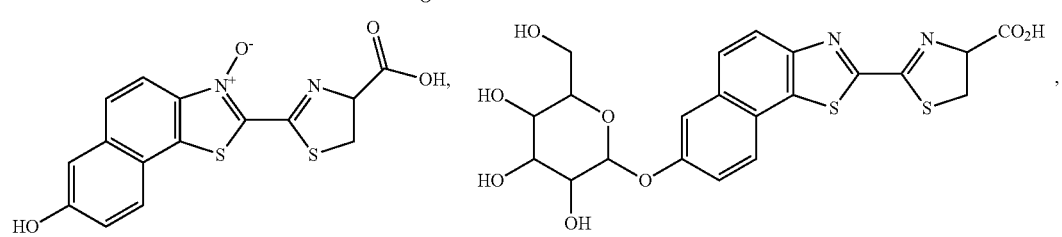
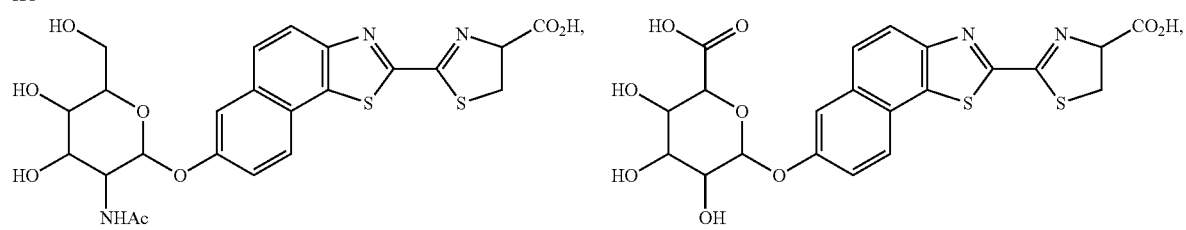

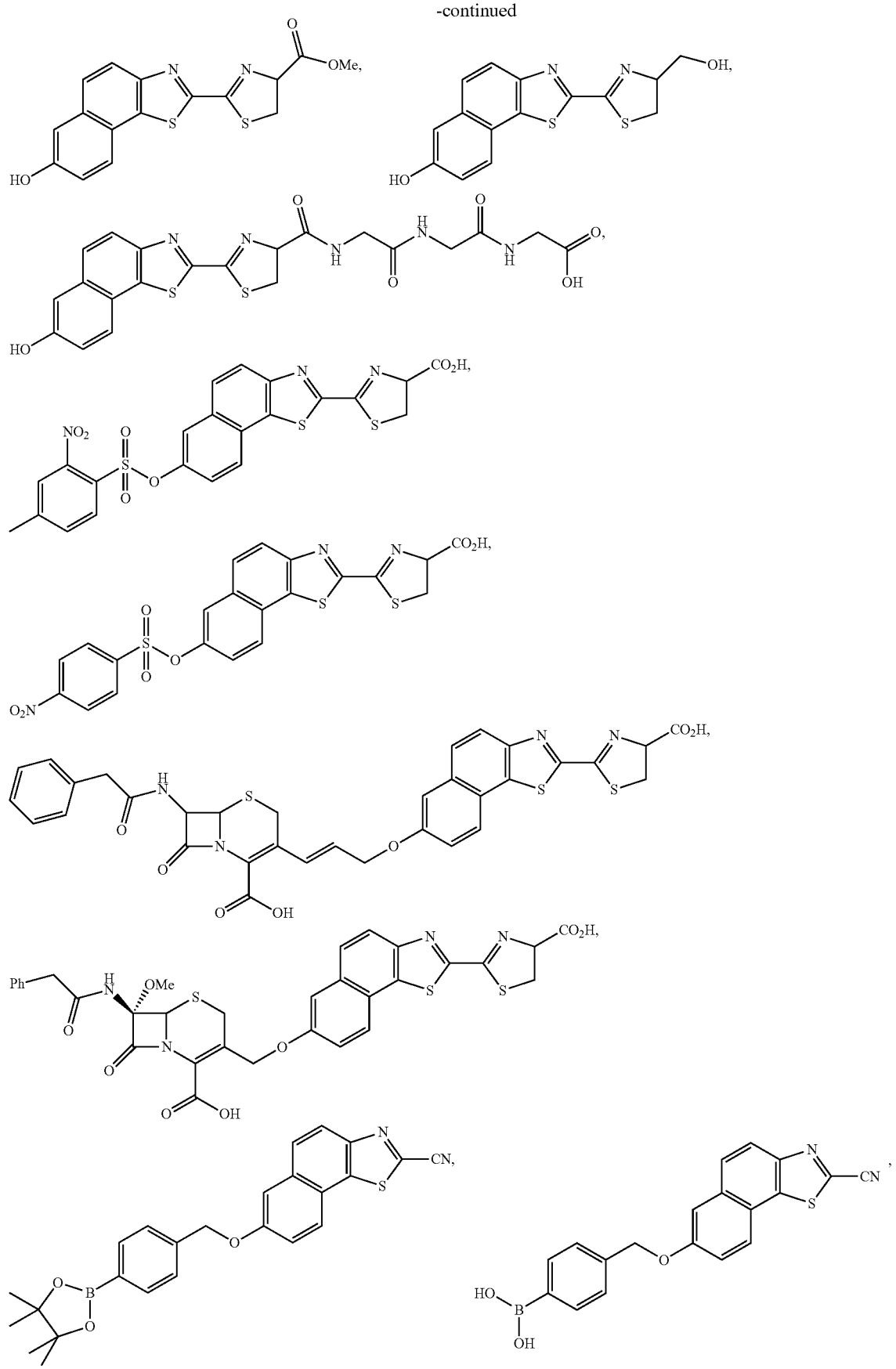

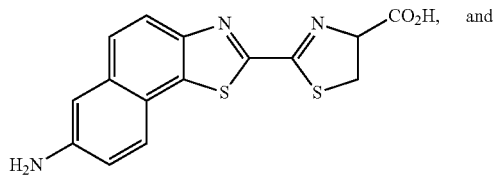 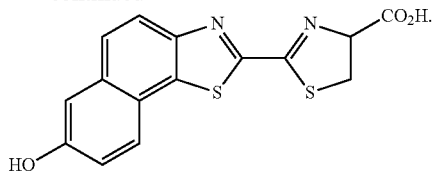
22. A compound according to claim 1, wherein the compound is a compound of Formula (VI):
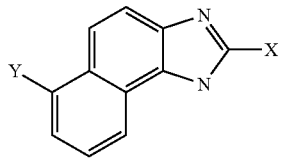
(VI)
wherein
X is CN or
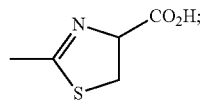
Y is $OR^1$ or $NR^1R^2$;
$R^1$ is H, $C_{1-10}$ alkyl or substituted $C_{1-10}$ alkyl; and
$R^2$ is H, $C_{1-10}$ alkyl or substituted $C_{1-10}$ alkyl; or
$R^1$ and $R^2$ together form a ring.
* * * * *